United States Patent
Singh et al.

(10) Patent No.: US 11,230,711 B2
(45) Date of Patent: Jan. 25, 2022

(54) INHIBITION OF LET7I AS A MEANS TO ENHANCE THE PROTECTIVE EFFECT OF PROGESTERONE AGAINST STROKE

(71) Applicant: UNIVERSITY OF NORTH TEXAS HEALTH SCIENCE CENTER, Fort Worth, TX (US)

(72) Inventors: Meharvan Singh, Benbrook, TX (US); Chang Su, Lucas, TX (US); Trinh Nguyen, Humble, TX (US)

(73) Assignee: UNIVERSITY OF NORTH TEXAS HEALTH SCIENCE CENTER, Fort Worth, TX (US)

( * ) Notice: Subject to any disclaimer, the term of this patent is extended or adjusted under 35 U.S.C. 154(b) by 6 days.

(21) Appl. No.: 16/639,139

(22) PCT Filed: Aug. 13, 2018

(86) PCT No.: PCT/US2018/046456
§ 371 (c)(1),
(2) Date: Feb. 14, 2020

(87) PCT Pub. No.: WO2019/036343
PCT Pub. Date: Feb. 21, 2019

(65) Prior Publication Data
US 2020/0216847 A1 Jul. 9, 2020

Related U.S. Application Data

(60) Provisional application No. 62/544,994, filed on Aug. 14, 2017.

(51) Int. Cl.
| | | |
|---|---|---|
| *A61K 31/713* | (2006.01) | |
| *A61K 38/18* | (2006.01) | |
| *C12N 15/113* | (2010.01) | |

(52) U.S. Cl.
CPC .......... *C12N 15/113* (2013.01); *A61K 31/713* (2013.01); *A61K 38/185* (2013.01); *C12N 2310/11* (2013.01); *C12N 2310/141* (2013.01); *C12N 2320/31* (2013.01)

(58) Field of Classification Search
CPC .............. C12N 15/113; C12N 2310/11; C12N 2310/141; C12N 2320/31; C12N 2310/113; A61K 31/713; A61K 38/185; A61K 31/57; A61K 31/7105; A61K 31/7088; A61P 25/28
See application file for complete search history.

(56) References Cited

U.S. PATENT DOCUMENTS

| | | |
|---|---|---|
| 2006/0185027 A1 | 8/2006 | Bartel et al. |
| 2016/0017329 A1 | 1/2016 | Esau et al. |
| 2016/0067244 A1 | 3/2016 | Leahy et al. |

OTHER PUBLICATIONS

Li et al. Inhibition of the Let-7 family micrornas induces cardioprotection against ischemia-reperfusion injury in diabetic rats. Ann Thorac Surg. (Year: 2016).*
Seeger et al. Inhibition of let-7 augments the recruitment of epicardial cells and improves cardiac function after myocardial infarction. J Mol Cell Cardiol.;94:145-152 May 2016.*
Ni, J. et al. "MicroRNA let-7c-5p protects against cerebral ischemia injury via mechanisms involving the inhibition of microglia activation" *Brain, Behavior, and Immunity*, 2015, pp. 75-85, vol. 49.
Selvamani, A. et al. "An Antagomirto MicroRNA Let7f Promotes Neuroprotection in an Ischemic Stroke Model" *PLoS ONE*, Feb. 2012, pp. 1-11, vol. 7, Issue 2, e32662.
Wendler, A. et al. "Involvement of let-7/miR-98 microRNAs in the regulation of progesterone receptor membrane component 1 expression in ovarian cancer cells" *Oncology Reports*, 2011, pp. 273-279, vol. 25.
Sorensen, S. S. et al. "miRNA expression profiles in cerebrospinal fluid and blood of patients with Alzheimer's disease and other types of dementia—an exploratory study" *Translational Neurodegeneration*, 2016, pp. 1-12, vol. 5, No. 6.
Mueller, M. et al. "PreImplantation factor promotes neuroprotection by targeting microRNA let-7" *PNAS*, Sep. 23, 2014, pp. 13882-13887, vol. 111, No. 38.
Balakathiresan, N. et al. "MicroRNA Let-7i is a Promising Serum Biomarker for Blast-Induced Traumatic Brain Injury" *Journal of Neurotrauma*, May 1, 2012, pp. 1379-1387, vol. 29.
Johnson, D. et al. "Acute and subacute microRNA dysregulation is associated with cytokine responses in the rodent model of penetrating ballistic-like brain injury" *Trauma Acute Care Surg.*, 2017, S145-S149, vol. 83, No. 1, Supplement 1.
Martinez, B. et al. "MicroRNAs as diagnostic markers and therapeutic targets for traumatic brain injury" Neural Regeneration Research, Nov. 2017, pp. 1749-1761, vol. 12, No. 11.
Di Pietro, V. et al. "MicroRNA Signature of Traumatic Brain Injury: From the Biomarker Discovery to the Point-of-Care" *Frontiers in Neurology*, Jun. 2018, pp. 1-15, vol. 9, Article 429.
Written Opinion in International Application No. PCT/US2018/046456, dated Oct. 19, 2018, pp. 1-6.

* cited by examiner

*Primary Examiner* — Kimberly Ballard
*Assistant Examiner* — Stacey N MacFarlane
(74) *Attorney, Agent, or Firm* — Saliwanchik, Lloyd & Eisenschenk

(57) ABSTRACT

The subject invention provides methods of treating neurological disease or disorder, such as brain injuries, such as stroke, traumatic brain injury (TBI), or other ischemic events that cause brain injury by inhibiting or down-regulating Let-7i activity or function. The disclosed methods may have the potential to extend the "window of opportunity" for treatment of such injuries and enhance the effectiveness of existing therapeutics.

7 Claims, 16 Drawing Sheets
(7 of 16 Drawing Sheet(s) Filed in Color)
Specification includes a Sequence Listing.

INHIBITION OF LET7I AS A MEANS TO ENHANCE THE PROTECTIVE EFFECT OF PROGESTERONE AGAINST STROKE

CROSS-REFERENCE TO RELATED APPLICATIONS

This application is the U.S. National Stage Application of International Patent Application No. PCT/US2018/046456, filed on Aug. 13, 2018, which claims the benefit of U.S. Provisional Application Ser. No. 62/544,994, filed Aug. 14, 2017, the disclosures of which are hereby incorporated by reference in their entirety, including all figures, tables and amino acid or nucleic acid sequences.

The Sequence Listing for this application is labeled "Seq-List.txt" which was created on Aug. 13, 2018 and is 1 KB. The entire content of the sequence listing is incorporated herein by reference in its entirety.

CROSS-REFERENCE TO RELATED APPLICATION

This application claims the benefit of U.S. Provisional Application Ser. No. 62/544,994, filed Aug. 14, 2017, the disclosure of which is hereby incorporated by reference in its entirety, including all figures, tables and amino acid or nucleic acid sequences.

GOVERNMENT SUPPORT

This invention was made with Government support under AG027956 awarded by the National Institutes of Health. The Government has certain rights in the invention.

BACKGROUND OF THE INVENTION

Stroke is the fourth leading cause of death and a major cause of disability in the US [14], costing approximately $34 Billion annually (according to the Center for Disease Control). The risk of ischemic stroke dramatically increases with age. Of note, the incidence of ischemic stroke is relatively rare among pre-menopausal women [1]. Although middle aged women have a lower risk of stroke than men, stroke becomes more prevalent in post-menopausal women compared to men of the same age [1]. With increasing age, circulating gonadal hormone levels decline in both males and females, however, such age-associated decreases are much more dramatic in women, and is a function of the menopause. While much attention has been placed on the loss of estrogen following the menopause, it is worth noting that the levels of P4 also decline precipitously. As such, the increased risk for stroke in postmenopausal women may be due to a decline in not just estrogen levels, but that of P4 as well. In fact, growing literature has suggested that P4 is protective, and is (neuro)protective in a variety of experimental models of stroke [2-4]. However, the underlying mechanisms for P4's protective effects remain unclear. It is this incomplete information that limits our understanding of why P4's beneficial effects were equivocal in the latest Phase III clinical trial of P4 efficacy in treating traumatic brain injury, despite numerous other studies (both preclinical and clinical) that demonstrate its positive efficacy. We suggest that a better understanding of the factors that influence the expression of key mediators (e.g., receptors) of P4 is critical to advancing the development of effective P4-based neuroprotectants.

It is also worth pointing out that the literature associated with P4's protective effects has focused on a direct effect of P4 on neurons. The notion that glia may be an equally important target underlying P4's protective effects on the brain has only been studied minimally. Indeed, astrocytes have been considered as an important component in the post-ischemic recovery, as these cells are critical for regeneration and remodeling of neural circuits following stroke [9].

A known mediator of P4's neuroprotective action is brain-derived neurotrophic factor (BDNF) [15]. A deficit in BDNF has been linked to stroke pathophysiology [16, 17]. In the central nervous system (CNS), BDNF also has an established role in promoting neuronal differentiation, survival, synaptic plasticity [6-8] and synaptogenesis [18-20]. Synaptogenesis occurring in the penumbra is known to strongly contribute to enhanced functional recovery from stroke [21-24]. Based on these observations, it is plausible that the P4/BDNF signaling-mediated enhanced synaptogenesis and neuroprotection may contribute to P4's protective effects during post stroke brain repair. We recently reported that P4 elicits the release of BDNF from primary astrocytes via a putative membrane progesterone receptor consisting of progesterone-receptor-membrane-component-1 (Pgrmc1) [10]. Our results suggest that conditioned medium derived from P4-treated astrocytes, when applied to primary cortical neurons, increases the expression of synaptic markers in these neural cells and enhances their survival against oxidative stress. Our data support the model whereby P4 elicits its (neuro)protective effects through a mechanism that involves Pgrmc1-dependent BDNF release from glia.

Currently, knowledge regarding the regulation of Pgrmc1 in brain and the consequence of such regulation is limited. Studies from our lab demonstrate that the miRNA, let-7i, negatively regulates expression of both Pgrmc1 and BDNF in glia, leading to suppression of P4-induced BDNF release from glia and attenuation of P4's beneficial effects on neuroprotection and synaptogenesis in the ischemic brain. Furthermore, the increased expression of let-7i with stroke may explain why post stroke therapy may not be so effective. As there remains a significant need for treatments of brain injuries, such as stroke and traumatic brain injury (TBI), down-regulation of let-7i may have the potential to extend the "window of opportunity" for treatment of such injuries.

BRIEF SUMMARY OF THE INVENTION

The neuroprotective effects of P4 have been reported since 1996 [25], however, knowledge of what governs the protective effects of P4 is still largely lacking. Further, a heavy emphasis has been placed on P4's "genomic" mechanism(s) of action, elicited via the classical progesterone receptor (PR), and that too, focused on neurons. However, evidence from emerging literature as well as from our own recent studies have highlighted the critical role of glia, both as a site of local P4 synthesis and as a mediator of P4's pro-survival functions in CNS [26-28]. The subject invention provides methods of treating neurological disease or disorder, such as brain injuries, such as stroke, traumatic brain injury (TBI), or other ischemic events that cause brain injury by inhibiting or down-regulating Let-7i activity or function. The disclosed methods may have the potential to extend the "window of opportunity" for treatment of such injuries and enhance the efficacy of existing treatments for such injuries.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1A represents immune-staining of Gap43 (green) and Synaptophysin (red). FIG. 1B represents qRT-PCR analysis of Gap43 (left) and Synaptophysin (right) mRNA levels. Data are presented as a percentage of control (non-treated group) (*: $p \leq 0.05$, **: $p \leq 0.01$).

(FIG. 8B) Quantitation of BDNF release measured by BDNF in situ ELISA (n=4). n.s: not significant compared to DMSO group. Data are presented as mean±SEM.

(FIG. 10A) Representative confocal images of primary cortical neurons (DIV 14) immunostained with synaptophysin (SYP, green) and DAPI (blue). (60×, Scale bars=30 µm). (FIG. 10B) Quantification of average number of SYP puncta per neuron (n=3). n.s: not significant, *$P<0.001$ compared to mock transfected+DMSO group. (FIG. 10C) Representative immunoblots probed for SYP and quantification graph of relative SYP protein ratio to Gapdh (n=4). n.s: not significant, $P<0.0001$, *$P<0.001$ compared to mock transfected+DMSO group. Data are presented as the mean±SEM.

(FIG. 11A) Representative immunoblots probed for Pgrmc1, pro- and mature-BDNF. (FIG. 11B) Quantitation graph of relative Pgrmc1 protein ratio to Gapdh (n=4-5 per group). (FIG. 11C) Quantitation graph of relative pro-BDNF protein ratio to Gapdh (n=4-5 per group). (FIG. 11D) Quantitation graph of relative mature BDNF protein ratio to Gapdh (n=4-5 per group). (FIG. 11E) Quantitation graph of relative let-7i expression in ischemic brain (n=4-5 per group). n.s: not significant, ** $P<0.01$ and *$P<0.05$ compared to sham, and #$P<0.05$ compared to P4+scrambled. Data are presented as the mean±SEM.

(FIG. 12A) Representative images of serial coronal brain sections stained with triphenyltetrazolium chloride (TTC). (FIG. 12B) Quantification of infarct sizes of TTC-stained images (n=4 per group). n.s: not significant, *$P<0.001$ and  $P<0.01$ compared to cholesterol+scrambled group. Data are presented as the mean±SEM.

(FIG. 14A) Representative confocal images of penumbra region staining for synaptophysin (SYP, red) and DAPI (blue). (60×, Scale bars=30 µm). (FIG. 14B) Quantification of average relative SYP puncta presents in each field (n=3 per group). n.s: not significant and *$P<0.001$ compared to sham, ### $P<0.001$ and ##$P<0.01$ compared to P4+scrambled. (FIG. 14C) Representative immunoblots probed for SYP protein. (FIG. 14D) Quantification graph of Syp signal, expressed as a ratio to Gapdh (n=4-5 per group). n.s: not significant, *$P<0.001$ and **$P<0.01$ compared to sham, ## $P<0.01$ and #$P<0.05$ compared to P4+scrambled.

DETAILED DISCLOSURE OF THE INVENTION

Figure 1A:
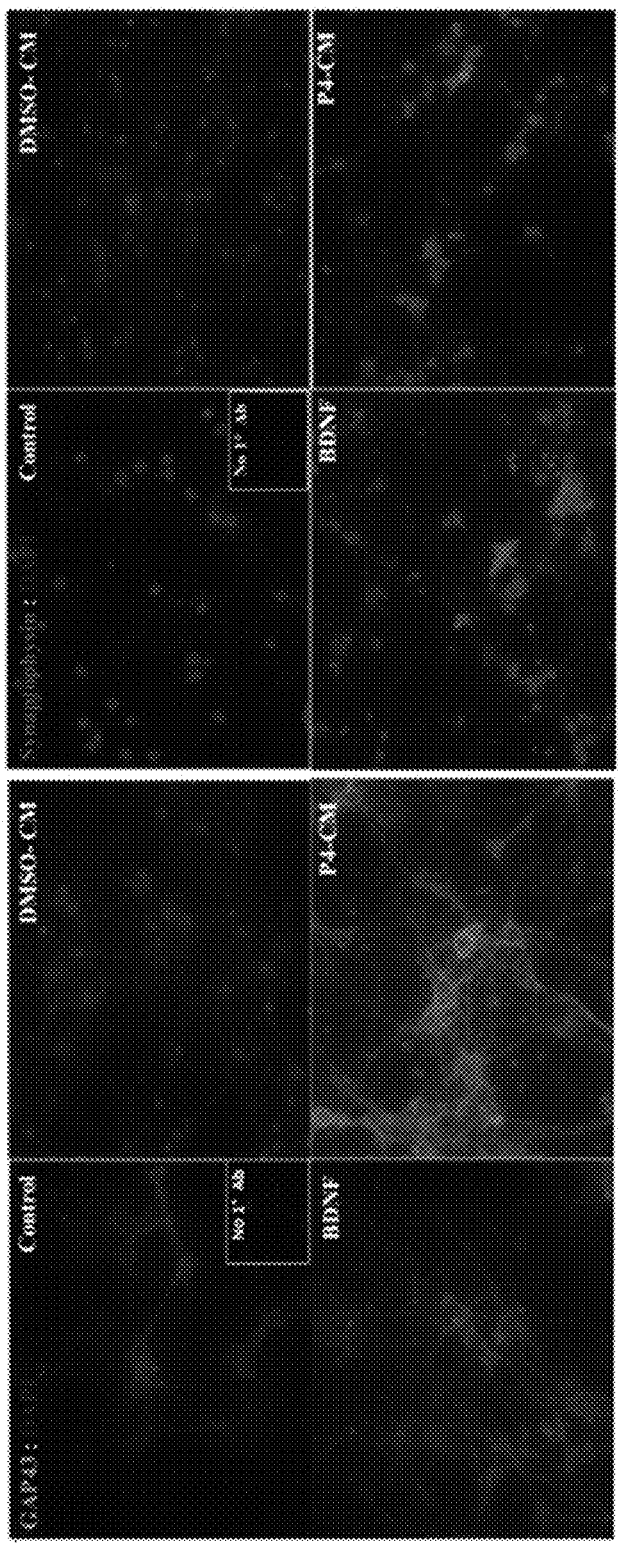
FIGS. 1A-1B: Conditioned medium derived from P4 (10 nM)-treated astrocytes (P4-ACM, 18 hrs) and BDNF (50 ng/ml, 18 hrs) increased expression of Synaptophysin and Gap-43 in primary cortical neurons.

The terminology used herein is for the purpose of describing particular embodiments only and is not intended to be limiting of the invention. As used herein, the singular forms "a", "an" and "the" are intended to include the plural forms as well, unless the context clearly indicates otherwise.

Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value.

As used herein, the "Let-7i" sequence comprises:
mmu-let-7i-5p MIMAT0000122
5' UGAGGUAGUAGUUUGUGCUGUU 3' (SEQ ID NO: 1). The let-7i-5p sequence is identical for both the human (MIMAT0000415) and murine (MIMAT0000122) miRNA. The full length human and murine let-7i sequences, including the stem loop can be obtained at the miRBase database (mirbase.org) as accession numbers MI0000434 (human, SEQ ID NO: 2) and MI0000138 (murine, SEQ ID NO: 3).

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), short hairpin RNA (shRNA), and silencing RNA (siRNA). Inhibitory oligonucleotides and vectors for delivering inhibitory oligonucleotides for Let-7i are commercially available from vendors such as Vigene Biosciences, Inc. (Rockville, Md. 20850 USA), OriGene Technologies, Inc. (Rockville, Md. 20850 USA), and Santa Cruz Biotechnology, Inc. (Dallas, Tex. 75220 USA).

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register", that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophores, etc.), being lipophilic, inducing special secondary structures like, for example, alanine containing peptides that induce alpha-helices.

As used herein "BDNF" and "Brain derived neurotrophic factor" are inclusive of all family members, mutants, alleles, fragments, species, coding and noncoding sequences, sense and antisense polynucleotide strands, etc. As used herein, the terms "Brain derived neurotrophic factor", "Brain-derived neurotrophic factor" and BDNF, are considered same in the literature and are used interchangeably in the present application.

"Progesterone" includes all natural forms of progesterone as well as chemically synthesized analogs of progesterone.

As used herein, the term "oligonucleotide specific for" or "oligonucleotide which targets" refers to an oligonucleotide having a sequence (i) capable of forming a stable complex with a portion of the targeted gene (in this case let-7i), or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

RNA interference "RNAi" is mediated by double stranded RNA (dsRNA) molecules that have sequence-specific homology to their "target" nucleic acid sequences (in this case let-7i). In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non-limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

The term "nucleotide" covers naturally occurring nucleotides as well as non-naturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in Benner et al., U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Kornberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) Nucl. Acid. Res., 25(22), 4429-4443, Toulme, J. J., (2001) Nature Biotechnology 19:17-18; Manoharan M., (1999) Biochemica et Biophysica Acta, 1489:117-139; Freier S. M., (1997) Nucleic Acid Research, 25:4429-4443, Uhlman, E., (2000) Drug Discovery & Development, 3: 203-213, Herdewin P., (2000) Antisense & Nucleic Acid Drug Dev., 10:297-310); 2'-O, 3'-C-linked [3.2.0] bicycloarabinonucleosides. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick, Hoogsteen or reversed Hoogsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15M) of salts with inorganic cations such as Na+ or K+ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1.times. sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense compound which is 18 nucleotides in length having 4 (four) non-complementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison, Wis.), using default settings, which uses the algorithm of Smith and Waterman (Adv. Appl. Math., 1981, Vol. 2, pp. 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

The terms "mammal", "patient" or "subject" covers warm blooded mammals that are typically under medical care (e.g., humans and domesticated animals). Examples include feline, canine, equine, bovine, and human, as well as only human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

In general, methods of administering compounds, including nucleic acids, are well known in the art. In particular, the routes of administration already in use for nucleic acid therapeutics, along with formulations in current use, provide preferred routes of administration and formulation for the nucleic acids described above. Compositions disclosed herein can be administered by a number of routes including, but not limited to: oral, intravenous, intracranial, intracerebro-ventricular, intraperitoneal, intramuscular, transdermal, subcutaneous, topical, sublingual, or rectal means. The disclosed compositions can also be administered via liposomes or other nanoparticles (e.g., packaged microsomes). Such administration routes and appropriate formulations are generally known to those of skill in the art.

Accordingly, the subject invention provides methods of treating neurological disease or disorder comprising administering an antagonist of Let-7i to a subject having a neurological disease or disorder. In various embodiments, the neurological disease or disorder is selected from: severance of nerves or nerve damage, severance of cerebrospinal nerve cord (CNS) or CNS damage, damage to brain or nerve cells, traumatic brain injury, spinal cord injury, stroke, hypoxia, ischemia, brain injury, diabetic neuropathy, aging, neurodegenerative disease (such as Alzheimer's disease, Parkinson's disease or dementia), peripheral neuropathy, or peripheral nerve injury. Antagonists of Let-7i include antisense oligonucleotides, siRNA, shRNA, or interfering RNA that downregulate or inhibit Let-7i activity or function. The inhibition of Let-7i function or activity can be mediated by degradation of the Let-7i miRNA when antisense oligonucleotides, siRNA, shRNA, or interfering RNA specifically hybridize with Let-7i. In various additional embodiments, the disclosed methods of treatment can, optionally, include the method the administration of progesterone or a composition thereof to said subject. The subject method can also further comprise the administration of BDNF to said subject. Antagonists of Let-7i, progesterone, BDNF and compositions thereof can be administered to a subject as independent compositions sequentially (e.g., a composition comprising one of more Let-7i antagonist, a composition comprising progesterone and/or a composition comprising BDNF) or as a combined composition (i.e., a compositions comprising one or more antagonist of Let-7i, progesterone, and/or BDNF).

Where the subject invention is used to treat signs of aging in a subject, for example, cognitive, behavioral and functional consequences of aging in the nervous system are to be treated. These include, and are not limited to: (a) changes in memory, (b) alterations of language function, (c) visual-perceptual changes, (d) slowing of reaction time, and/or (e) decreased balance and coordination. One or more of these consequences of aging in the nervous system may be treated.

Following are examples which illustrate procedures for practicing the invention. These examples should not be construed as limiting. All percentages are by weight and all solvent mixture proportions are by volume unless otherwise noted.

EXAMPLE 1

General Methods:

Generation of Primary Neuron- or Glia-Enriched Cultures:

The use of animals for the purpose of generating primary cultures was approved by the Institutional Animal Care and Use Committee at the University of North Texas Health Science Center. All mice will be handled according to the Guide for the Care and Use of Laboratory Animals. Primary cultures of cortex and hippocampal neurons will be prepared from neonatal murine pups (C57BL/6 mice, Jackson Laboratory) as described by Sarkar et al. with modifications [22, 41]. Briefly, cortical tissues isolated from newborn mice (postnatal days 2-4, mixed gender) will be then dissociated with trypsin and DNase I for 10 min at 37° C., and wash twice with Neurobasal-A medium containing B-27 and further dissociated by gentle titration using a graded series of fine polished Pasteur pipettes. After centrifugation at 200×g for 3 min at 4° C., dissociated cells will be resuspended in Neurobasal-AB-27 medium, passed through a cell strainer with 70 μm mesh, and plated at 1.0×105 cells/cm2 on culture dishes precoated with poly-D-lysine. The culture dishes were kept at 37° C. in humidified 95% air and 5% CO2. For primary neuron-enriched culture, the initial culture medium was replaced after 5 h; subsequently, half of the medium was changed every 3 days. At day in vitro (DIV) 3, 1-β-arabinofuranosylcytosine (AraC) was added to a final concentration of 5 μM to prevent glial proliferation. Treatments of the primary neuronal cultures started at DIV 14. For glial-enriched cultures, confluent mixed glial cultures were placed on the shaker for 48 hrs to dislodge microglia, resulting in cultures enriched with astrocyte population.

Quantitative RT-PCR (microRNA):

Total RNA was isolated from primary astrocytes and mouse brains using the MiRNeasy Mini Kit (QIAGEN, Valencia, Calif.) according to the manufacturer's instructions. Concentrations of extracted RNA were determined using absorbance values at 260 nm. The purity of RNA was assessed by ratios of absorbance values at 260 and 280 nm (A260/A280 ratios of 1.9-2.0 were considered acceptable). Total RNA (10 ng) was reverse transcribed into cDNA in a total volume of 15 μl using the High-Capacity DNA Archive Kit (Roche Applied Science, Indianapolis, Ind.) according to the manufacturer's instructions. The reaction mixture contained water, 2× quantitative PCR Master Mix (Eurogentec, Freemont, Calif.), and 20× Assay-On-Demand for each target gene. A separate reaction mixture was prepared for the endogenous control, U6. The reaction mixture was aliquoted in a 96-well plate, and cDNA added to give a final volume of 20 μL. Each sample was analyzed in triplicate. The comparative cycle threshold (Ct) method (2-ΔΔCt) was used to calculate the relative changes in target gene expression.

BDNF Immuno Assay In Situ:

To define the amount of endogenous BDNF released, we will modify the ELISA in situ protocol developed by Promega. A 96-well Nunc MaxiSorp surface polystyrene flat-bottom immunoplate was precoated with an anti-BDNF monoclonal antibody [diluted 1:1,000 in coating buffer (25 mM sodium bicarbonate and 25 mM sodium carbonate, pH 9.7)]. After rinsing off unbound antibody with TBS-T buffer [20 mM Tris-HCl (pH 7.6), 150 mM NaCl and 0.05% (v/v) Tween-20] and blocking the plate to minimize nonspecific binding, the culture media was added to the plate for 2 hrs to equilibrate the cell growth environment. Primary astrocytes were then plated, and after a period of time to ensure cell attachment to the plate, the appropriate treatments were applied. BDNF standards, ranging in concentration from 1.95 to 500 pg/ml, was added in parallel wells. At the end of hormone treatment, cells were carefully washed with TBST. The plate was then incubated with the polyclonal anti-human BDNF antibody. The amount of specifically bound polyclonal antibody was then detected through the use of the anti-IgY-horseradish peroxidase (HRP) tertiary antibody (final concentration=0.5 μg/mL), which when exposed to the chromogenic substrate (TMB reagent; Promega), changes color in proportion to the amount of BDNF present in the sample. The color intensity was quantified by measuring the absorbance at 450 nm with a Viktor3 ELISA plate reader (Perkin Elmer). Only values within the linear range of the standard curve, and above the lowest standard, were considered valid. BDNF levels were normalized to protein and are reported as a percentage of vehicle control. This method allowed detection of as little as 2 pg/ml BDNF release in control cultures to ~250 pg/ml in P4-treated cultures.

Ovariectomy:

Mice will receive bilateral ovariectomy (OVX) using a dorsal approach under isoflurane anesthesia. A small cut is made through skin and abdominal muscles in left and right lateral abdomen. The arteries to left and right ovaries will be ligated, and ovaries will be cut. The muscles and skin will be sutured with 4-0 Vicryl absorbable suture.

Implantation of Flash-Fused Steroid Pellets:

Fused steroid pellets will be made using the flash-melt method described by Ratka and Simpkins [40]. The pellets (containing P4 or control) will be implanted subcutaneously into abdominal area.

Transient Middle Cerebral Artery Occlusion (MCAo):

MCAo will be used to induce transient focal cerebral ischemia (as previously described [41]). Briefly, under isoflurane anesthesia, a mid line incision will be made on the neck. Common carotid artery (CCA), external carotid artery (ECA) and internal carotid artery (ICA) will be dissected from the connective tissue. A silicon coated 6-0 nylon monofilament will be inserted into the left ECA and advanced till it occludes the origin of MCA. The MCA will be occluded for 60 minutes and then reperfusion attained by withdrawing the suture.

ICV (Intracerebroventricular) Antagomir Injections:

ICV injections will be performed as described by Sananbenesi et al. [42]. In brief, mice will be anaesthetized and affixed with a cannula ipsilateral to the side of surgery (coordinates from Bregma: AP1/4_0.4 mm, L1/4_1.15 mm, V1/4_2.0 mm). Mice will receive a 0.5 uL infusion of Let-7i-silencing antagomir (Exiqon, Vedbaek, Denmark) or scrambled antagomir (5 ug), in artificial cerebrospinal fluid (Harvard Apparatus).

The Pole Test:

Animals will be trained 2 days before MCAo procedure and will be tested on day 3, 7, and 14 post stroke. Training will be achieved by placing animals facing downward on the pole and allow them to descend. After repeating this training 5 times, animals will then be trained in the regular turning and descending procedure. Mice will be placed on the rod facing upward. Normally, animals will turn around and start descending themselves. Those that do not, however, can be encouraged to turn by gently pushing to a side. After each trial, mice will be allowed to explore the cage for 15 s and then returned to their home cage. An interval of at least 5 min will be allowed between trials. Mice will tested 3 trials and average performance is recorded.

The Wire Hanging Test:

Animals will be trained 2 days before MCAo procedure and will be tested on day 3, 7, and 14 post stroke. Animals will be allow to suspend their bodies on a single wire stretched between 2 posts 50 cm above the ground. Between the posts, a soft pillow will be placed to avoid injury in case of a fall. Training will be achieved simply with several rounds of habituation and trials. In the actual testing phase, mice will be tested 3 times and average performance is recorded as final values.

Statistical Analysis:

We anticipate a minimal sample size (i.e., "n") of 4 per group in aim 1 studies and an "n" of 13 per group in aim 2 studies. This number of sample size is based on the following parameters: Detecting a minimal effect size of 20%, setting alpha=0.05, and a desired power of 80% or greater. Data (densitometric analysis for Western blotting, or numerical data from cell viability assays and from synapse quantification assays) will be analyzed using analyses of variance (ANOVA) followed by analysis of differences between individual groups using Tukey's post-hoc tests. Relative abundance of miRNA and mRNA transcripts will be evaluated using the $2^{(-\Delta\Delta Ct)}$ method [43]. Resulting data will be analyzed using Dunnett's test to compare fold change in the experimental groups relative to the control group.

Figure 1B:
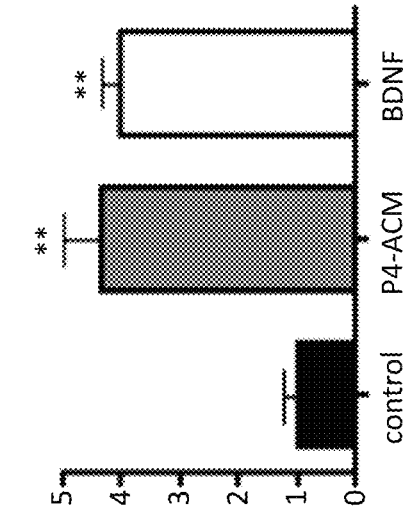
Figure 1B:
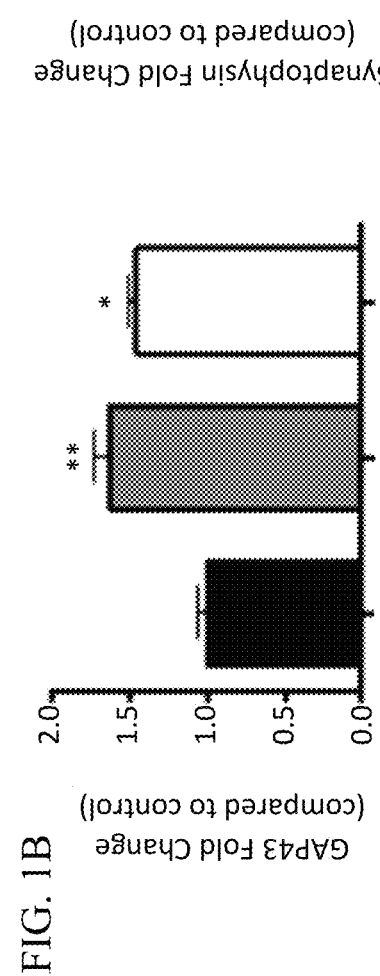

Both purified BDNF and conditioned medium derived from P4-treated astrocytes increased the expression of synaptic markers in neurons: Synaptogenesis has been considered as an important mechanism for functional recovery after stroke [21, 29, 30]. P4 has been shown to induce synaptogenesis in various brain locations, including cortex and hippocampus [4, 31, 32]. Although the underlying mechanism remains unclear, one potential mediator for P4-induced synaptogenesis is BDNF [33]. Our preliminary data showed that both conditioned media derived from P4-treated mouse primary astrocyte cultures and purified recombinant BDNF increased the expression of synaptophysin (a presynaptic terminal marker, usually overexpressed during the neuronal remodeling [34]) and GAP43 (a synaptic marker that is mainly synthesized during axonal outgrowth during neuronal development and regeneration [7]) in primary cortical neurons (FIGS. 1A-1B). Increased expressions of both markers have been linked to P4-induced synaptogenesis following stroke [4]. In conjunction with our previous work demonstrating that P4-induced BDNF release from glia is dependent on Pgrmc1 [10], this data supports that P4-induced increase in expression of synaptic markers is mediated, at least in part, by the Pgrmc1-dependent release of BDNF from glia.

Figure 2B:
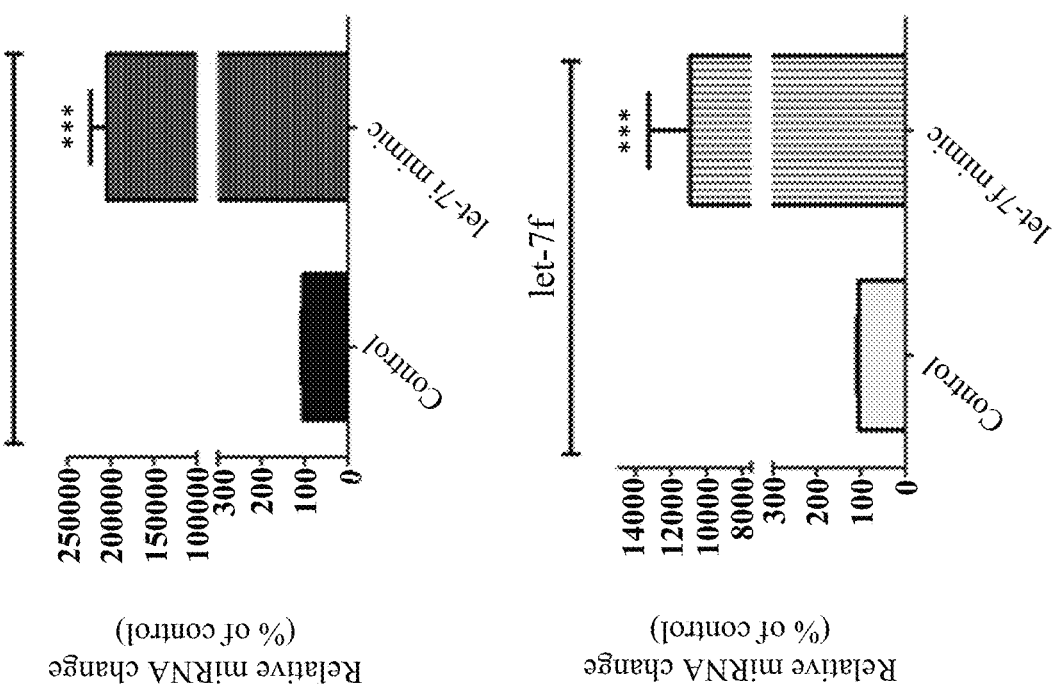
FIGS. 2A-2B: Over-Expression of Let-7i down-regulated Pgrmc1 and BDNF mRNA in primary astrocytes. Cells were transfected with let-7i or let-7f mimic or a negative control 48 hrs prior to RNA isolation for qRT-PCR. Quantification of Pgrmc1 and BDNF mRNA levels was normalized to GAPDH (FIG. 2A). Quantification of let-7 levels was normalized to U6 snRNA (FIG. 2B). Data are presented as a percentage of control (***: $p \leq 0.001$, n.s: non-significant).
Figure 2A:
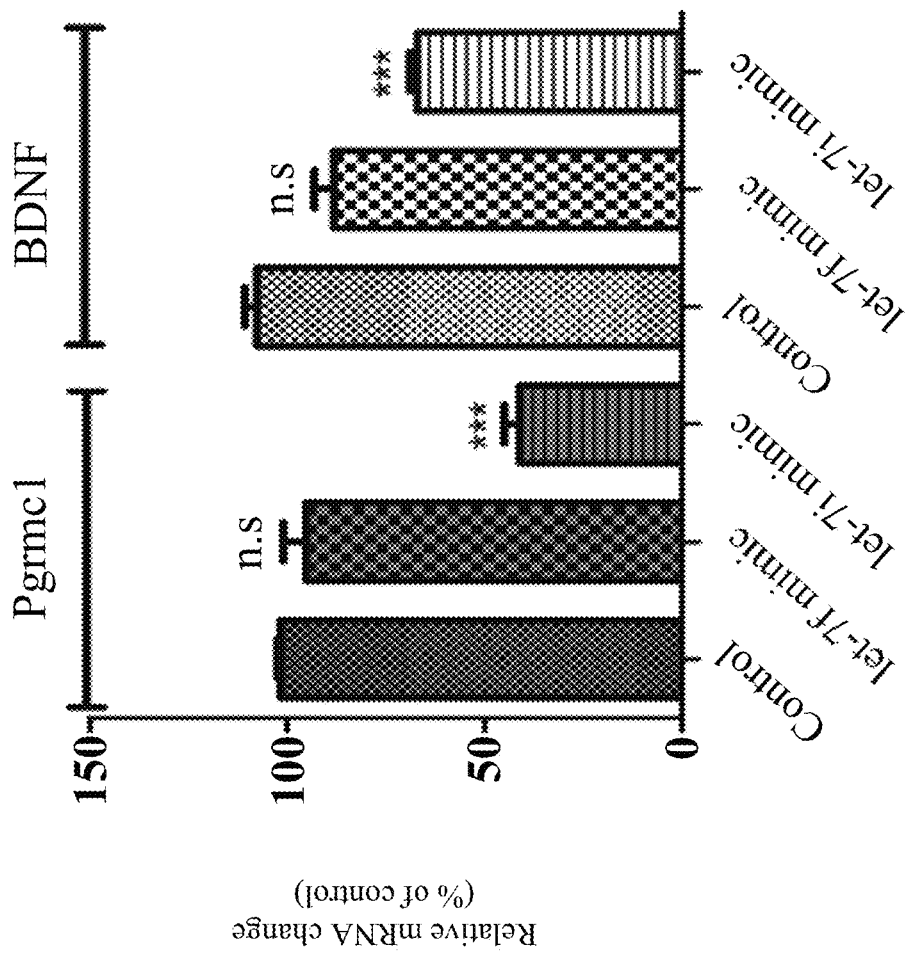

Overexpression of Let-7i Decreased Pgrmc1 and BDNF mRNA in Primary Astrocytes:

An in silico analysis, using three prediction software programs (miRDB, TargetScan and microRNA.org), revealed putative Let-7 binding sites in the 3'-UTR of Pgrmc1 and BDNF that were conserved in rat, mouse and human sequences. The Let-7 family of miRNAs includes multiple evolutionarily conserved members (Let-7a, b, c, d, e, f, g, i; miR-98) that can exert similar functions [35]. Since it has been reported that miRNA Let-7i directly binds to the 3'-untranslated terminal region (UTR) of Pgrmc1 mRNA, thereby repressing Pgrmc1 expression in a peripheral (non-CNS) cell type [36], we chose to focus on let-7i in this study and used another let-7 family member, let-7f, as a control for specificity. Our data show that in primary cortical astrocytes, an overexpression of the let-7i mimic (synthetic double-stranded miRNA-like RNA fragment), but not the let-7f mimic, resulted in decreased Pgrmc1 and BDNF mRNA levels (FIGS. 2A-2B), supporting the notion that Let-7i negatively regulates Pgrmc1/BDNF system in glia.

Figure 3:
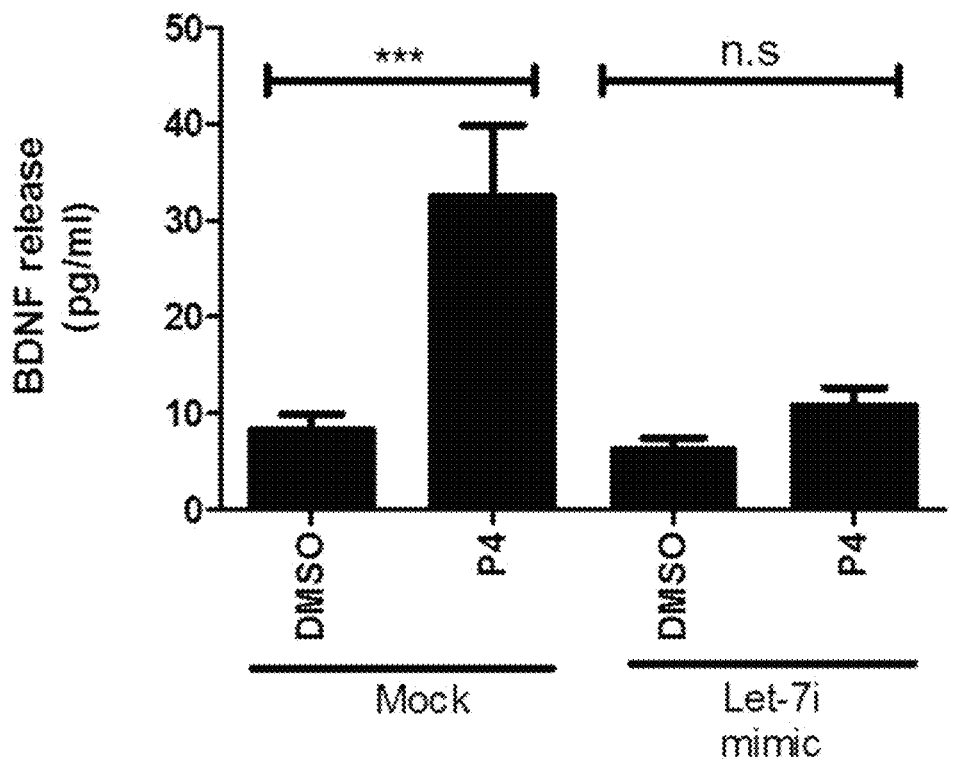
FIG. 3: Let-7i attenuates P4-induced BDNF release from primary cortical astrocytes, measured by in-situ BDNF ELISA (***: $p \leq 0.001$, n.s: non-significant).

Overexpression of Let-7i Attenuated P4-Induced BDNF Release from Primary Astrocytes:

FIG. 3 demonstrates that overexpression of let-7i abolished P4-induced BDNF release from primary cortical astrocytes. We previously showed that P4 triggered significant release from glia by acting via Pgrmc1 [10]. When considering data in both FIGS. 2A-2B and 3, they support our experimental model that states that let-7i inhibits P4-induced BDNF release from glia by down-regulating expression of both Pgrmc1 and BDNF.

Figure 4:
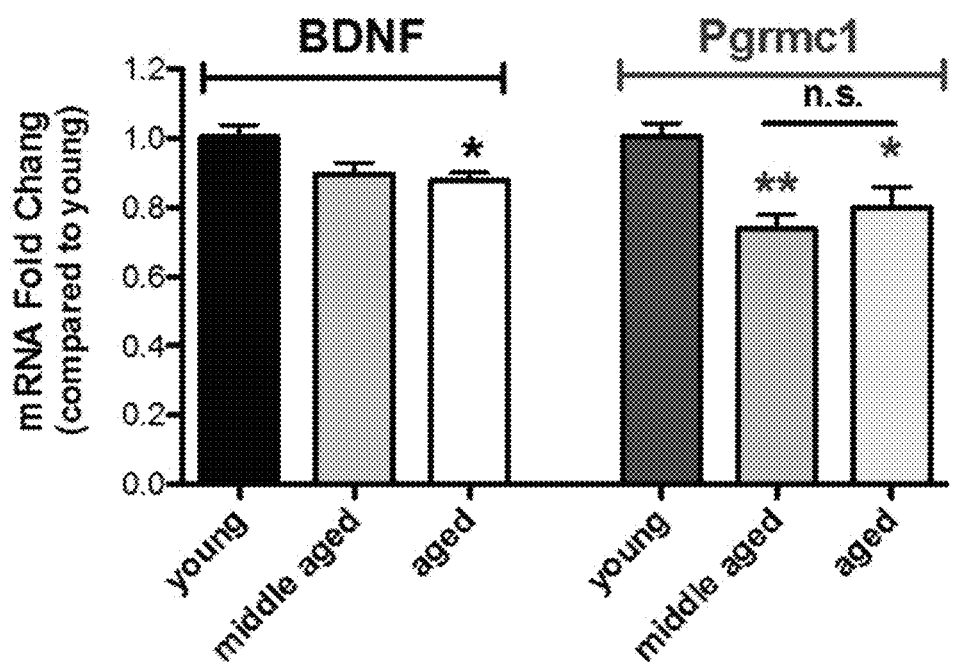
FIG. 4: Age-related decrease of Pgrmc1 expression correlated with decrease of BDNF in mouse hippocampus. mRNA levels were measured by qRT-PCR (young: 6-mo old; middle-aged: 12-mo old; old: 24-mo old. Data presented as a percentage of young group (*: $p \leq 0.05$, **: $p < 0.01$, n.s: non-significant).

Expression of Pgrmc1 and BDNF Decrease as the Function of Age in Mouse Brain:

Current literature lacks information regarding the effects of age on the expression of Pgrmc1 within the brain. Interestingly, we found an age-associated decrease of Pgrmc1 and BDNF mRNA in mouse hippocampus (FIG. 4). The decline in Pgrmc1 level was noted in middle-aged mice, and preceded the decrease of BDNF in old animals. Since Pgrmc1 is required for P4-induced BDNF release from glia, decrease of Pgrmc1 expression during normal aging may dampen P4's neuroprotective effect. Moreover, such a decline in Pgrmc1 (and BDNF) may also explain the increased risk for stroke in older individuals.

Figure 5A:
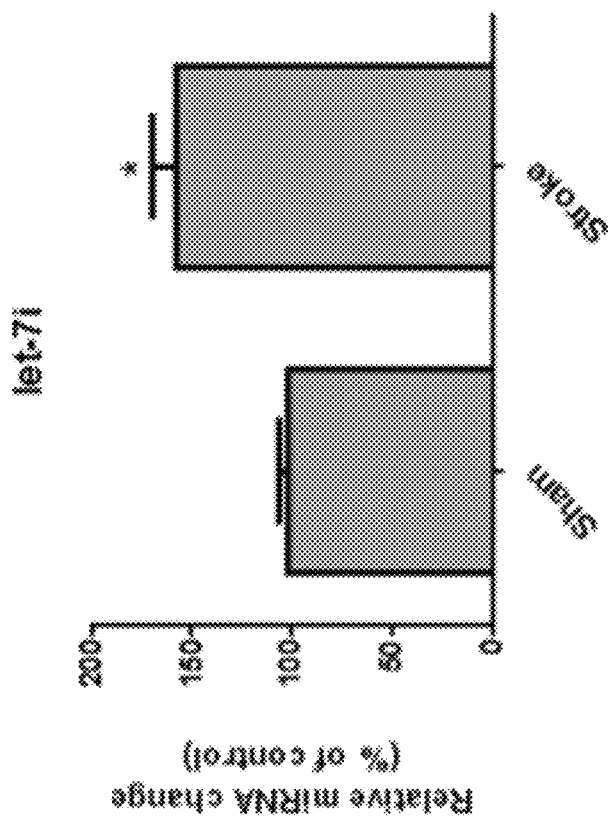
FIGS. 5A-5B: A decrease of Pgrmc1 expression correlates with an increase of Let-7i in cortex at day 7 post-stroke. Total RNA was measured by qRT-PCR. Pgrmc1 mRNA was normalized to GAPDH (FIG. 5A). Let-7i expression was normalized to U6 snRNA (FIG. 5B) (*: $p \leq 0.05$).
Figure 5B:
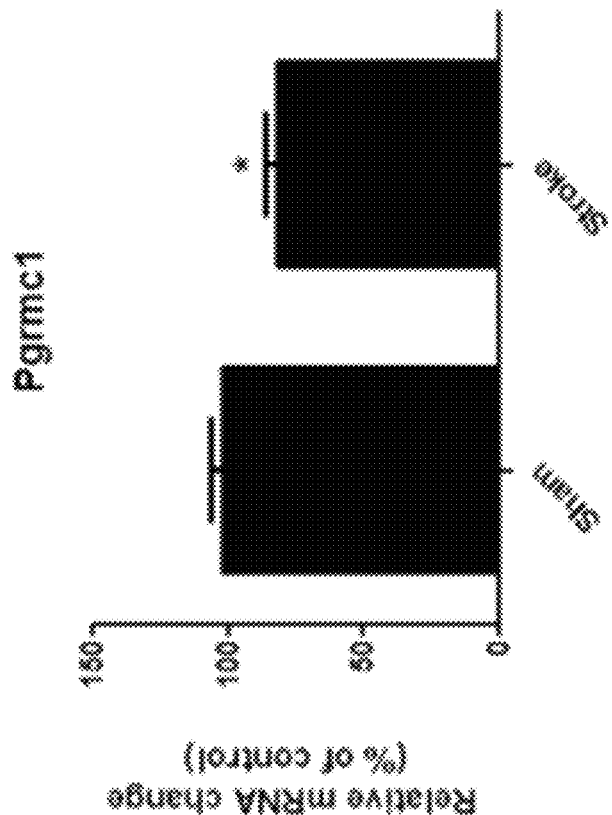

A decreased expression of Pgrmc1 correlates with an increased expression of let-7i in the cerebral cortex following an experimentally-induced ischemic stroke: To determine the potential involvement of let-7i in stroke, we induced an ischemic stroke in C57/B16 female mice using the method of middle cerebral artery occlusion (MCAo), then we examined expression of the miRNA in the cerebral cortex 7 days post stroke. FIG. 5 shows that, compared to sham group, expression of let-7i increases by about 60% in stroked animals, which correlated with a decreased in Pgrmc1 expression. Data from FIGS. 2A-2B and 5A-5B support our conclusion that let-7i represses expression of Pgrmc1. The data also support our use of the MCAo method as a suitable model to study the regulation of let-7i/Pgrmc1/BDNF axis in ischemic stroke.

Our data show that let-7i negatively regulates expression of Pgrmc1 and BDNF in primary astrocytes and there is an inverse correlation between let-7i and BDNF/Pgrmc1 in the ischemic brain. Therefore, we anticipated that BDNF and Pgrmc1 will be elevated following intracerebro-ventricular (ICV) injection of anti-let-7i, relative to the scrambled control. P4 is known to reduce infarct size, reverse functional deficits, and induce synaptogenesis in experimental stroke models [3, 37]. Therefore, we predicted that mice exposed to P4 will show an increase in synaptogenesis in the penumbra, smaller ischemic lesion and hence, a positive functional recovery (demonstrated by measures of motor function, to include the wire-hanging test). ICV injection of the Let-7i antagomir under conditions of stroke was thus, expected to reverse the suppression of glial Pgrmc1/BDNF pathway, thereby, contributing to an enhanced P4-induced upregulation of synaptogenesis, smaller ischemic lesion and enhanced motor function. The scientific literature suggests that synaptogenesis in the penumbra significantly increases within hours of stroke and can last for several weeks [23, 24, 38]. Therefore, we examined a window of 0-14 day post MCAo to monitor synaptogenesis both acute and intermediate time points. We used a published protocol for the delivery of microRNA to the central nervous system [39], to ensure that anti-let-7i ICV injection result in sufficient miRNA knock-down that would lead to an observable effect on synaptogenesis and neuroprotection.

Figure 6:
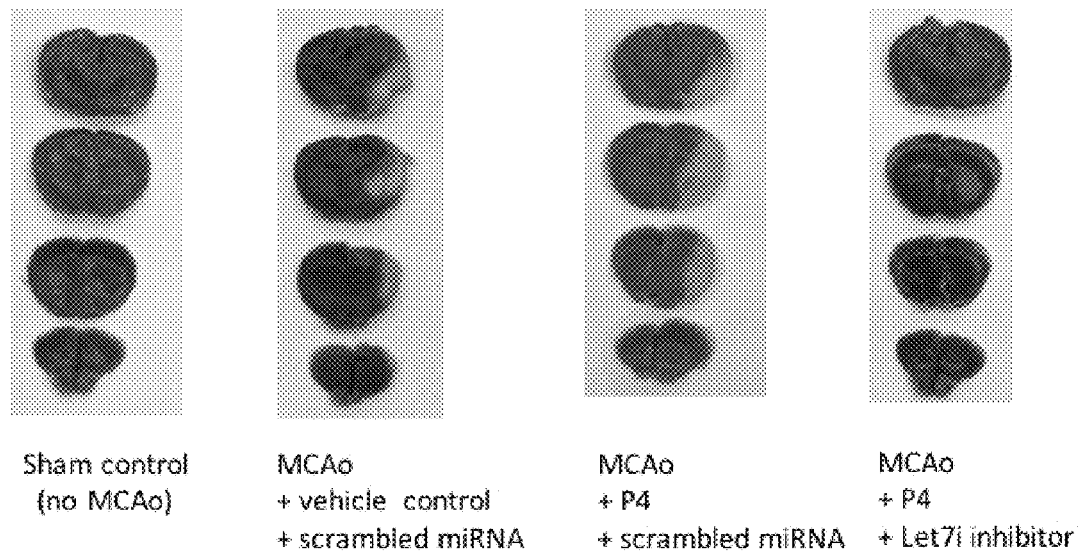
FIG. 6: Ischemic injury is greatly reduced in animals receiving P4 and the Let-7i inhibitor.

FIG. 6 shows the effect of co-administration of the Let-7i antagomir and P4 on the stroke-induced lesion size. Areas of damaged/dead cells appear white, whereas live tissue appears red, as a function of metabolism of the TTC stain. Compared to animals that were not subject to sham surgery (i.e., all aspects of the surgery were conducted, except the occlusion of middle cerebral artery—1$^{st}$ column of sections representing rostral (top most) to caudal (bottom most) aspects of the brain), the induction of stroke (2$^{nd}$ column of sections) showed obvious ischemic damage. P4 had no statistically significant effect. Remarkably, the co-application of Let-7i and P4 led to a near complete protection from the ischemic stroke.

Figure 7:
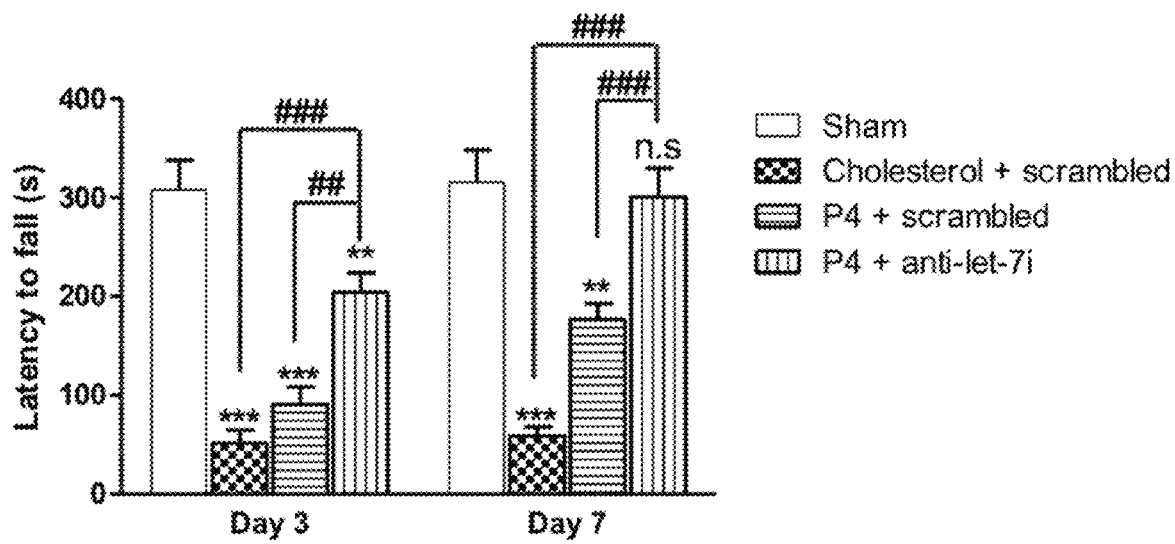
FIG. 7: Functional recovery (grip strength) is greatly enhanced in animals receiving ICV injections of the Let-7i inhibitor.

FIG. 7 shows the functional recovery in the same four groups of animals depicted in FIG. 6. Functional recovery of motor function, as defined by an assessment of grip strength, revealed that the combination of both the Let-7i antagomir and P4 led to complete functional recovery 7 days post treatment.

EXAMPLE 2

Materials and Methods

Primary Cultures:

Dissociated cortical neurons were prepared and maintained as previously described (44). Briefly, cortices were removed from neonatal mouse brains (postnatal day 2-4, mixed gender) and dissociated with 0.25% trypsin. Cortical neurons were then plated on glass coverslip or plastic culture dishes coated with poly-D-lysine (Sigma). The culture medium used was Neurobasal (ThermoFisher Scientific), supplemented with Glutamax and B27 serum-free supplement (ThermoFisher Scientific). At day in vitro (DIV) 3, 5 µM final concentration of 1-β-arabinofuranosylcytosine (45) (Sigma) was added to the neuronal cultures to prevent glial proliferation. Half of the medium was replaced with fresh medium every four days. For viability assay, cortical neurons were plated onto 96-well plates (Corning) at the concentration of $1.2 \times 10^5$ cells/cm$^2$. For immunocytochemistry, cortical neurons were plated onto 12 mm glass coverslip (Neuvitro) at the density of $4 \times 10^4$ cells/cm$^2$. Treatments of primary cortical neurons started at DIV12.

Primary cortical astrocytes were prepared and maintained as previously described (46), with some modifications. Briefly, cortices of post-natal day 2-4 mouse pups were dissociated with 0.25% trypsin and plated onto 75 cm$^2$ tissue culture flask. The culture medium used was Dulbecco's modified Eagle's medium (DMEM) (ThermoFisher Scientific), supplemented with 10% fetal bovine serum (FBS) (GE Healthcare Life Sciences) and 10000 U/ml Penicillin-Streptomycin (ThermoFisher Scientific). After reaching confluence, mixed glial cultures were placed on the shaker for 48 h to dislodge microglia, resulting in cultures enriched with astrocyte population.

Treatment of Primary Cultures:

To determine the miRNA regulation of downstream targets in primary cortical astrocytes, miRNA mimics and inhibitors were transfected into these cells for 48 hrs. After transfection, total RNA and proteins were isolated for gene and protein expression analysis. Mock transfection was used as the control for these experiments.

To study the effect of miRNA on P4-induced BDNF release from astrocytes, BDNF in-situ ELISA were performed. Expression of miRNA was first manipulated by transfection as described above. 24 h after transfection, 10 nM P4 was added to primary cortical astrocytes for additional 24 h without changing media containing transfection complexes. Vehicle controls were performed in parallel such that control cultures were exposed to 0.1% dimethylsulfoxide (DMSO). The 10 nM concentration of P4 used in studies described here was chosen because it has been reported to elicit a maximal release of BDNF from astrocytes (10).

In experiments evaluating the effect of miRNA on P4-induced neuroprotection and the synaptogenic marker, synaptophysin, we first transfected miRNA mimic and inhibitor into primary cortical astrocytes for 24 h. Afterward, P4 (10 nM) was added to these cultures for additional 24 h to generate P4-treated-astrocytes-derived-conditioned-media (P4-ACM). In parallel, treatment of 0.1% DMSO was performed to generate DMSO-treated-astrocytes-derived-conditioned-media (DMSO-ACM), which served as vehicle controls. Before applying to primary neurons, these conditioned media were filtered through a 10 kD cut-off column to eliminate residual P4 and miRNA mimic or inhibitor. In neuroprotection assay, astrocytes-conditioned-media were added to primary cortical neurons with prior exposure to one hour of oxygen-glucose-deprivation (OGD), an in-vitro model of ischemic-like insult. Based on our experience, 1 h of OGD was enough to induce 50% neuronal cell death. BDNF (50 ng/ml) was directly added to different groups after OGD to serve as positive control. Neuronal cultures exposed to normoxia were used as the control for these data sets. 24 h after the applications of BDNF or conditioned-media, CellTiter-Glo Luminescent cell viability assay (Promega) was performed to measure neuroprotection. In synaptogenic marker measurement assay, BDNF and astrocytes-derived-conditioned-media were directly added to primary cortical neurons for 24 hrs. Synaptophysin expression and number of synaptophysin puncta in these neuronal cultures were assessed by immunocytochemistry, followed by confocal imaging and analyzed using ImageJ (National Institutes of Health) software (47).

Transfection:

Transfection of miRNA mimics and inhibitors was performed using the Hiperfect transfection reagent (Qiagen) according to manufacturer's instructions. Cells were transfected with miRNA mimics and inhibitors for 48 h. This duration was chosen since it resulted in an optimal effect on targets-of-interest. Synthetic miRNA mimics (Syn-mmu-let-7i-5p, Syn-mmu-let-7f-5p) and inhibitors (Anti-mmu-let-7i-5p, Anti-mmu-let-7f-5p) were purchased from Qiagen.

Quantitative RT-PCR:

Total RNA was isolated from primary cortical astrocytes and mouse brains using the MiRNeasy Mini Kit (Qiagen) according to the manufacturer's instructions. Concentrations of extracted RNA were determined using absorbance values at 260 nm. The purity of RNA was assessed by ratios of absorbance values at 260 and 280 nm (A260/A280 ratios of 1.9-2.0 were considered acceptable).

For miRNA expression measurements, total RNA (10 ng) was reverse transcribed into cDNA in a total volume of 15 µl using the microRNA cDNA Archive Kit (ThermoFisher Scientific) according to the manufacturer's instructions. The reaction mixture contained water, 2× quantitative PCR Master Mix (Eurogentec), and 20× Assay-On-Demand for each target gene. A separate reaction mixture was prepared for the endogenous control, U6. The reaction mixture was aliquoted in a 96-well plate, and cDNA added to give a final volume of 20 µl. Each sample was analyzed in triplicate. The comparative cycle threshold (Ct) method ($2^{-\Delta\Delta Ct}$) was used to calculate the relative changes in target miRNA expression.

For mRNA expression measurements, total RNA (1.6 µg) was reverse transcribed into cDNA in a total volume of 20 µl using the High-Capacity cDNA Archive Kit (ThermoFisher Scientific) according to the manufacturer's instructions. The reaction mixture contained water, 2× quantitative PCR Master Mix (Eurogentec), and 20× Assay-On-Demand for each target gene. A separate reaction mixture was prepared for the endogenous control, GAPDH. The reaction mixture was aliquoted in a 96-well plate, and cDNA (30 ng RNA converted to cDNA) was added to give a final volume of 30 µl. Each sample was analyzed in triplicate. The comparative cycle threshold (Ct) method ($2^{-\Delta\Delta Ct}$) was used to calculate the relative changes in target gene expression.

PCR primers were purchased as Assay-On-Demand from ThermoFisher Scientific.

The assays were supplied as a 20 mix of PCR primers (900 nM) and TaqMan probes (200 nM). The let-7i (002221), U6 (001973), BDNF (Mm00432069_m1), GAP-43 (Mm00500404_m1), GAPDH (Mm99999915_g1), PSD-95 (Mm00492193 ml), Pgrmc1 (Mm00443985_m1) and SYP (Mm00436850_m1) assays contain FAM (6-carboxyfluorescein phosphoramidite) dye label at the 5' end of the probes and minor groove binder and nonfluorescent quencher at the 3' end of the probes.

CellTiter-Glo Luminescent Cell Viability Assay (Promega):

This assay uses the level of adenosine triphosphate (48) as an indicator of metabolically active cells and is directly proportional to the number of living cells (49, 50). The assay was performed according to manufacture's instruction. In brief, cell plate was first equilibrated to room temperature for 30 minutes. A volume of the kit reagent equal to the volume of cell culture present was then added to each well. The plate was then placed on an orbital shaker for 2 minutes to induce cell lysis, followed by 10 minutes of incubation at room temperature. Luminescence was recorded using a plate reader.

BDNF Immuno Assay In Situ:

To determine the amount of endogenous BDNF released with P4 treatment, we performed ELISA in situ assay, as previously described (10). In brief, a 96-well Nunc MaxiSorp surface polystyrene flat-bottom immunoplate was pre-coated with an anti-BDNF monoclonal antibody [diluted 1:1,000 in coating buffer (25 mM sodium bicarbonate and 25 mM sodium carbonate, pH 9.7). After blocking nonspecific binding, primary cortical astrocytes were then plated, followed by appropriate treatments application. BDNF standards, ranging in concentration from 1.95 to 500 pg/ml, was added to parallel wells. At the end of hormone treatment, cells were carefully washed with TBST. The plate was then incubated with the polyclonal anti-human BDNF antibody. The amount of specifically bound polyclonal antibody was then detected through the use of the anti-IgY-horseradish peroxidase (HRP) tertiary antibody, which when exposed to the chromogenic substrate (TMB reagent, Promega), changes color in proportion to the amount of BDNF present in the sample. The color intensity was quantified by measuring the absorbance at 450 nm with a Viktor3 ELISA plate reader (Perkin Elmer). Only values within the linear range of the standard curve, and above the lowest standard, were considered valid. This method allowed detection of as little as 2 pg/ml BDNF release in control cultures to ~250 pg/ml in P4-treated cultures.

Oxygen-Glucose Deprivation (OGD):

OGD was performed according to an established protocol, as described elsewhere, with minor modifications (51). Briefly, primary cortical neurons were carefully washed five times with Hank's balanced salt solution (HBSS, ThermoFisher Scientific) to remove residual glucose. Glucose-free DMEM (ThermoFisher Scientific) was then added to the cultures, and the plates were transferred into a hypoxic chamber (0.1% oxygen) for 1 h. At the end of hypoxia, glucose-free DMEM was replaced with regular maintaining media. Reoxygenation was initiated by transferring the cells to normoxic 5% CO2 cell culture incubator.

Western Blotting:

Primary cortical astrocytes and mouse brains were lysed with RIPA lysis buffer containing protease and phosphatase inhibitors, as previously described (44). After homogenization, samples were centrifuged at 45,000 rpm for 30 min at 4° C. and supernatants were collected. Total protein concentrations were determined using the Bio-Rad DC protein assay kit (Bio-Rad Laboratories). Cell lysates were separated by SDS-PAGE and transferred onto polyvinylidene fluoride membrane (Bio-Rad Laboratories) by electroblotting. Membranes were blocked with 5% skim milk in tris-buffered saline containing 0.2% Tween 20 (TBS-T) for 1 h at room temperature, followed by overnight incubations of primary antibodies at 4° C. The following primary antibodies were used: rabbit polyclonal anti-PSD 95 (1:1000, ab18258, Abcam), rabbit polyclonal anti-Synaptophysin (1:1000, ab14692, Abcam), rabbit monoclonal anti-GAP43 (1:200000, ab75810, Abcam), rabbit monoclonal anti-GAPDH (1:1000, 14C10, Cell Signaling), rabbit polyclonal anti-BDNF (1:300, sc546, Santa Cruz) and goat polyclonal anti-Pgrmc1 (1:500, ab48012, Abcam). After washing three times with TBS-T, membranes were incubated with anti-goat IgG or anti-rabbit IgG conjugated with horseradish peroxidase (Millipore) for 1 hr at room temperature. After triple washes with TBS-T, immunoreactive bands were visualized with the ECL detection system (ThermoFisher Scientific) and were captured using a luminescent image analyzer (Alpha Innotech). Densitometric analysis was conducted using ImageJ (National Institutes of Health) software (47).

Immunofluorescence:

The cortical neurons were fixed in 4% paraformaldehyde (45) for 15 min, followed by incubation in 0.2% Triton X-100 in Tris-buffered saline (TBS) for 15 min at room temperature for permeabilization. Cultures were then blocked with 5% donkey serum/1% bovine serum albumin (BSA) in TBS for 1 h at room temperature and incubated with rabbit monoclonal anti-Synaptophysin (1:500, ab32127, Abcam) for 48 h at 4° C. After extensive rinsing with TBS-Tween 20, cultures were incubated with Alexa Fluor 647-conjugated secondary antibody (1:500, Jackson ImmunoResearch Laboratories) for 2 h at room temperature. After extensive washing with TBS to remove unbound secondary antibody, the coverslips were mounted onto glass slides (VWR Scientific) using Vectashield mounting medium with DAPI (Vector Laboratories). The slides were observed under a confocal fluorescence microscope (FV1200, Olympus) with a 60× objective.

Mouse brains were fixed in 4% PFA overnight at 4° C. and subsequently cryoprotected in 30% sucrose solution. The brains were then sectioned into 40-µm thick coronal slices and subjected to immunostaining using an established protocol described elsewhere, with some modifications (52). In brief, brain sections were blocked in 5% donkey serum/1% BSA/TBS solution for 2 h at room temperature. In staining using mouse primary antibody, sections were subsequently blocked in F(ab) fragment donkey anti-mouse IgG (50 ug/ml, Jackson ImmunoResearch Laboratories) for 2 h at room temp to reduce background caused by secondary antibody binding to endogenous mouse IgG in the tissue. After blocking step, brain sections were then incubated in primary antibody solution at 4° C. for 72 h. Primary antibodies used were as follow: mouse monoclonal anti-NeuN (1:500, ab104224, Abcam); rabbit polyclonal anti-GFAP (1:1000, ab7260, Abcam); rabbit monoclonal anti-Synaptophysin (1:500, ab32127, Abcam) and goat polyclonal anti-Pgrmc1 (1:200, ab48012, Abcam). Alexa Fluor 647, Alexa Fluor 594 or Rhodamine Red-conjugated secondary antibodies (Jackson ImmunoResearch Laboratories) were used at 1:500 dilution. After immunostaining, sections were mounted onto microscope slides with Vectashield mounting medium (Vector Laboratories) and observed under a confocal fluorescence microscope (FV1200, Olympus) with a 63× objective.

Mice and Treatments:

All procedures with animals were reviewed and approved by the Institutional Animal Care and Use Committee of the University of North Texas Health Science Center. All institutional and federal guidelines for the care and the use of animals were followed. Female C57BL/6J mice (18-weekold) were purchased from Jackson Laboratory. Animals were habituated to housing conditions one week before experiments.

All mice were first ovariectomized to deplete endogenous ovarian hormone levels. Two weeks after ovariectomy (OVX), P4 pellets were subcutaneously implanted into these animals to replenish their progesterone levels. In parallel, different groups received cholesterol pellet implantations to serve as vehicle control. One week after pellet implantation, stroke was induced in these mice using middle cerebral artery occlusion (MCAo) procedure. In parallel, different groups received sham operation (non-stroke). 30 min after MCAo, 5 µg of either scrambled or let-7i inhibitor was injected into each animal brain via intracerebroventricular (ICV) injection. Experimental groups included sham-operated mice with cholesterol pellet implantation (sham), stroked mice with cholesterol pellet implantation and scrambled ICV injection (cholesterol+scrambled), stroked mice with P4 pellet implantation and scrambled ICV injection (P4+scrambled), and stroked mice with P4 pellet implantation and let-7i inhibitor ICV injection (P4+anti-let-7i).

Ovariectomy:

Bilateral ovariectomy (OVX) was performed using a dorsal approach under isoflurane anesthesia, as described elsewhere (53). Briefly, small incisions were made bilaterally to expose ovaries. The arteries adjacent to ovaries were ligated before ovaries removal. Incisions were then closed using 4-0 Vicryl absorbable suture.

Transient Middle Cerebral Artery Occlusion (MCAo):

MCAo was performed to induce transient focal cerebral ischemia, as previously described (54). In brief, mice were anesthetized with isoflurane inhalation. A mid-line incision was made on the neck. Left common carotid artery (CCA), external carotid artery (55) and internal carotid artery (ICA) were dissected from the connective tissue. The left MCA was occluded by a 6-0 monofilament suture (Doccol Corporation) introduced via internal carotid artery. After 45 minutes occlusion, the suture was withdrawn for reperfusion. In sham-operated animals, monofilament was advanced to MCA region and withdraw immediately without MCA occlusion.

Intracerebroventricular (ICV) injection:

5 µg of either scrambled or let-7i inhibitor (GE Healthcare Dharmacon) was suspended in 0.5 µL of PBS and injected into lateral ventricles using a stereotaxic instrument, as previously described, with minor modifications (56). In brief, the solution was injected using a 5-uL Hamilton syringe attached to the Ultra Micro Pump UMP3 system (World Precision Instruments) at a flow rate of 0.2 µl/min. Coordinates used for ICV injection were AP −0.58 mm, ML+1.2 mm, DV−2.1 mm.

Assessment of Brain Tissue Damage: 2,3,5-Triphenyltetrazolium Chloride (TTC) Staining:

TTC staining was performed to assess ischemic injury among groups, as described in an established protocol (57). Briefly, 24 h after MCAo, mouse brains were harvested and sectioned into 2-mm thick coronal sections. These sections were immersed in 2% TTC solution for 30 min at 37° C. and then fixed in 10% formalin. The stained slices were photographed and subsequently measured for the surface area of the slices and the ischemic lesion (Image-Pro Plus 3.0.1, Silver Springs, Md., U.S.A.). Imaged of stained sections were captured and infarct sizes were analyzed using ImageJ (National Institutes of Health) software (47).

Functional Recovery Assessment:

wire suspension test: In ordered to assess motor function recovery with different treatments, wire suspension test, a test of grip strength and endurance, was used, as described elsewhere (58). In brief, mice were allowed to suspend their bodies on a single wire that was elevated above a padded platform. The latency for animals to fall off the wire was recorded. Mice were trained two days prior to MCAo to establish a baseline across groups. Training was achieved with several rounds of habituation and trials. In the actual testing phase, each mouse was tested 3 times, and average performance was taken as final values. Performances of these mice was evaluated at day 3, 7 and 14 post stroke.

Synaptophysin (SYP) Optical Density Analysis and Puncta Quantification:

For experiments using primary cortical neurons, mounted coverslips were imaged using a confocal fluorescence microscope (FV1200, Olympus) with a 63× objective. Healthy cells that were at least two cell diameters from their nearest neighbor were identified and selected at random by eye by DAPI fluorescence. Ten non-overlapping fields per sample were imaged. Quantification of SYP immunoreactivity (IR) was performed using ImageJ (National Institutes of Health) software (47). Average IR was calculated by dividing total IR value by the number of cells presented in the captured image. Synaptophysin puncta quantification was analyzed with a custom plug-in (written by Barry Wark; available upon request from c.eroglu@cellbio.duke.edu) for ImageJ program. The details of this imaging and quantification method can be found in a previous publication (59).

To quantify SYP fluorescence intensity and number of puncta in mouse brain, three independent coronal brain sections per animal were stained with SYP. 5-µm confocal scans were performed (optical section width, 0.33 µm; 15 optical sections each) at 63× magnification, as previously described (60). Maximum projections of three consecutive optical sections corresponding to 1-µm sections were analyzed by using the ImageJ puncta analyzer option to quantify for numbers of SYP puncta (≥5 optical sections per brain section and ≥15 total images per brain). Average SYP puncta density per imaged area was calculated for each treatment group.

Statistical Analysis:

In vitro data obtained from no fewer than three independent experiments (where each independent experiment consisted of between 5-8 replicates), and in vivo data obtained from at least 4 animals per group (as many as 20 animals per group for the functional recovery/motor function tests) were analyzed using an analysis of variance (ANOVA), followed by appropriate post hoc analyses for the assessment of group differences, and presented as a bar graph depicting the mean±S.E.M, using the GraphPad Software (San Diego, Calif.). The parameters used to inform sample size considered the following: detecting an effect size of at least 30%, $\alpha=0.05$, the variance of the endpoint measured, and achieving a statistical power of at least 0.8.

Figure 8A:
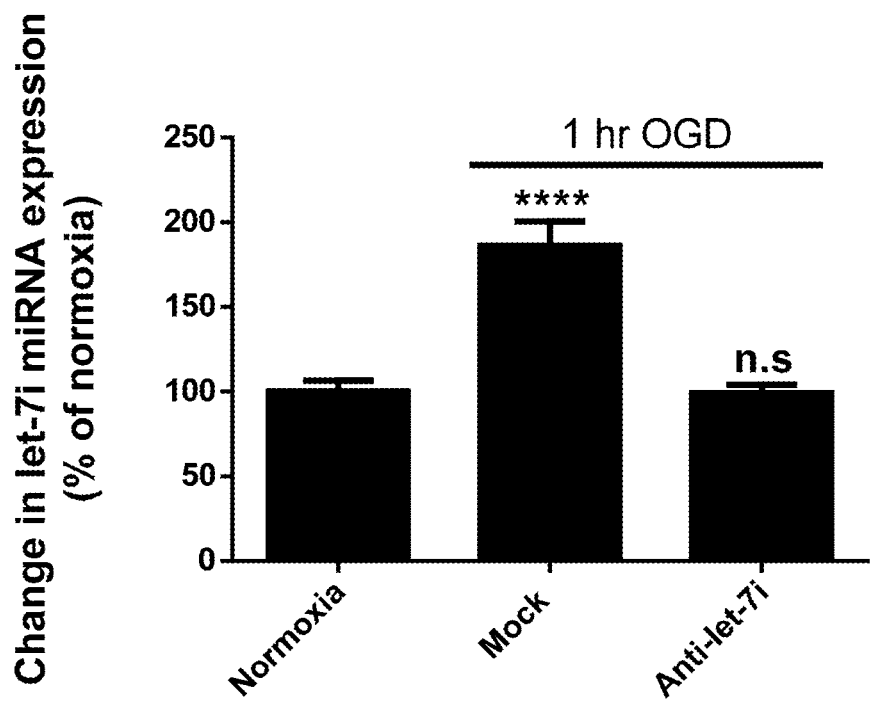
FIGS. 8A-8B: Oxygen-Glucose Deprivation (OGD) results in an increase in let-7i expression and suppresses progesterone (P4)-induced BDNF release from primary cortical astrocytes. Primary cortical astrocytes were exposed to one-hour of OGD. Immediately after re-instatement of normal oxygen and glucose concentrations, these cells were either mock transfected (control) or transfected with the let-7i antagomir. 12 hours later, expression of let-7i was evaluated (FIG. 8A) (n=4). n.s: not significant, ****$P<0.0001$ compared to mock transfected control (mock).
Figure 8B:
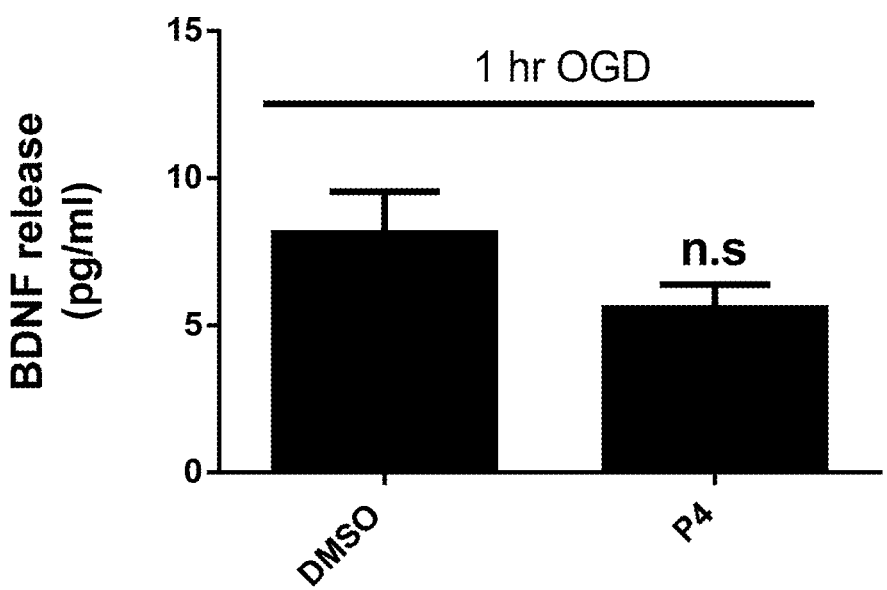

Let-7i Antagomir Inhibits Oxygen-Glucose-Deprivation (OGD) Induced Increase in Let-7i Expression:

Oxygen glucose deprivation (OGD), used in the primary cortical astrocytes as an in vitro model of ischemia, revealed an increase in let-7i expression. Importantly, the data also verified the effectiveness of the let-7i antagomir to attenuate the OGD-induced increase in let-7i expression (FIG. 8A). The data in FIG. 8B demonstrate that OGD (which increases let-7i expression) compromised the ability of progesterone (P4)-induced BDNF release from primary cortical astrocytes, similar to what was noted when let-7i was specifically over-expressed.

Figure 9:
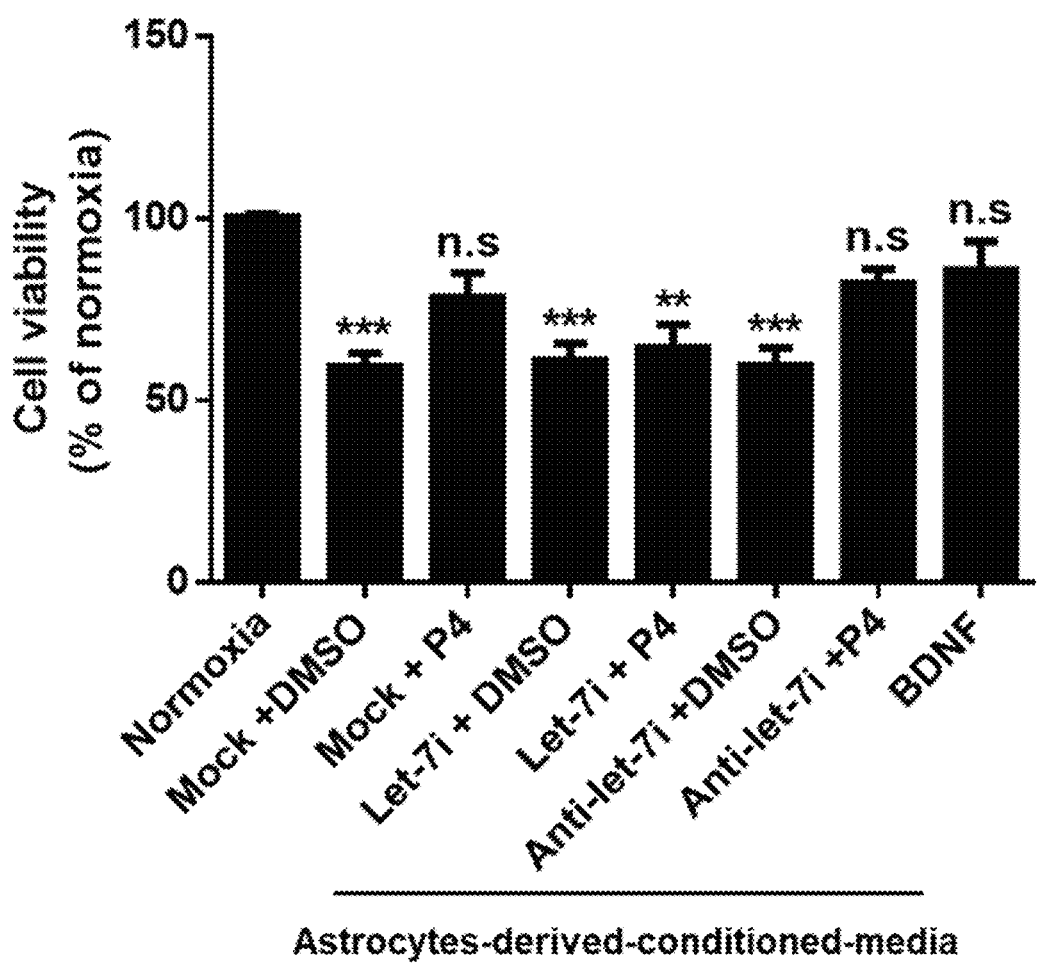
FIG. 9: let-7i prevents progesterone (P4)-induced neuroprotection against oxygen-glucose-deprivation (OGD). Conditioned-media derived from hormone or control-treated astrocytes were applied to primary cortical neurons (DIV 14) after one-hour exposure to OGD. BDNF (50 ng/ml) was directly added to neurons after OGD to serve as positive control. Neuronal viability was measured by CellTiter-Glo viability assay (n=5). n.s: not significant, *$P<0.001$ and $P<0.01$ compared to normoxia. Data are presented as the mean±SEM.

Let-7i Represses Progesterone (P4)'s Neuroprotection and its Enhancement on Synaptogenesis:

To investigate the role of let-7i in P4's neuroprotective effects, we manipulated miRNA expression in primary cortical astrocytes, then treated them with either vehicle (DMSO) or P4, following which astrocyte-derived conditioned media (ACM) was collected. The conditioned media was then applied to primary cortical neurons (days in vitro (DIV)14) that had been exposed to oxygen-glucose deprivation (OGD). The neurons were then assessed for cell viability to ascertain if conditioned media from P4-treated astrocytes elicited greater neuroprotection relative to neurons treated with conditioned media from DMSO-treated astrocytes (FIG. 9). We found that conditioned media collected from P4-treated astrocytes conferred similar neuroprotection as seen in the positive control group (consisting of direct administration of BDNF (50 ng/ml) to the neuronal cultures). However, conditioned media collected from P4-treated astrocytes that overexpressed let-7i failed to promote the protection of neurons from OGD.

Figure 10A:
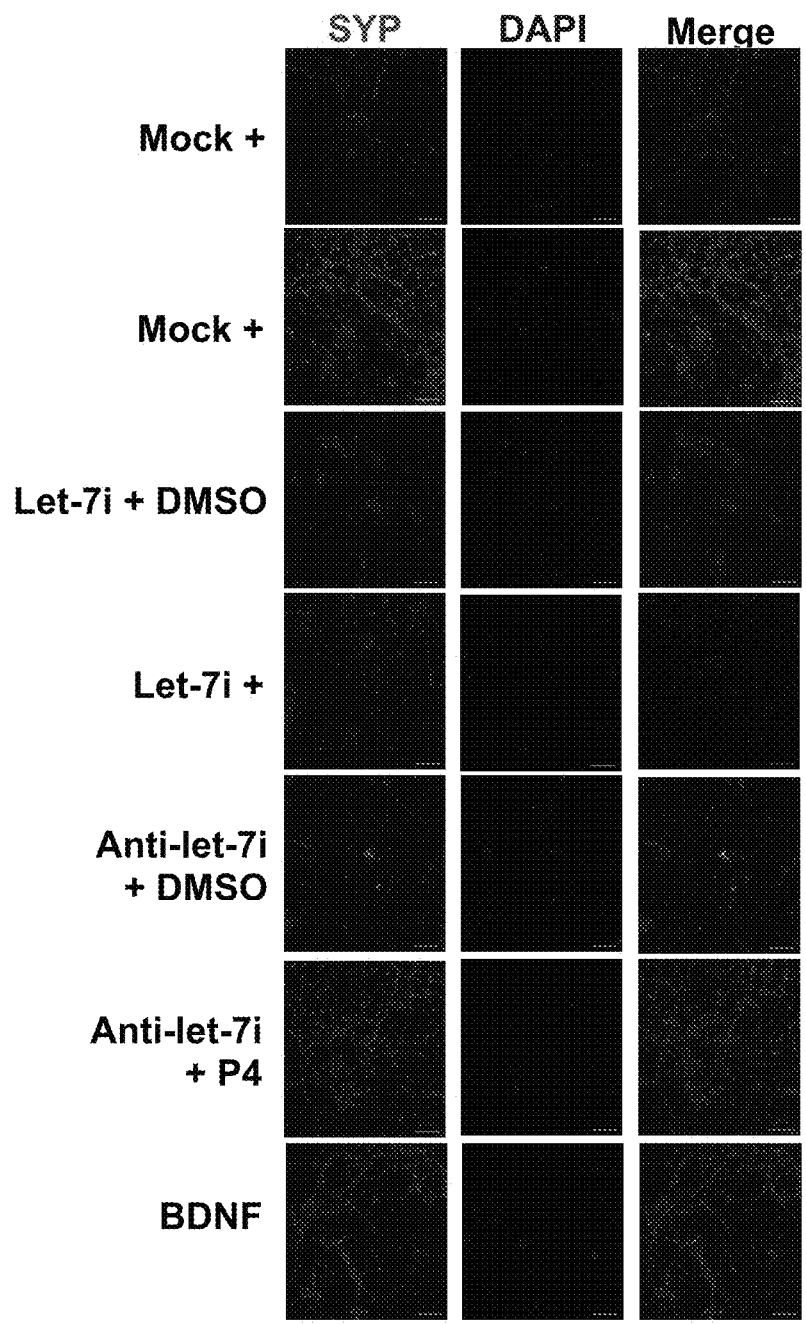
FIGS. 10A-10C. let-7i inhibits progesterone (P4) induces synaptophysin (SYP) expression in primary cortical neurons.
Figure 10B:
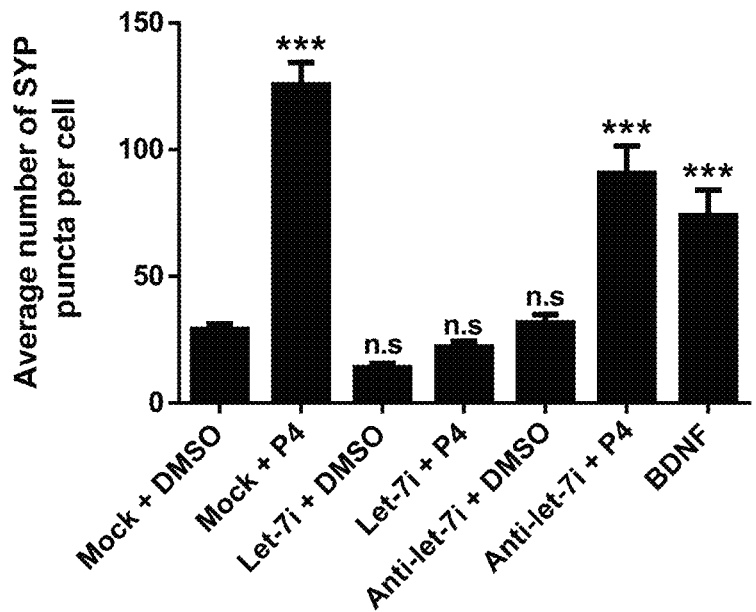
Figure 10C:
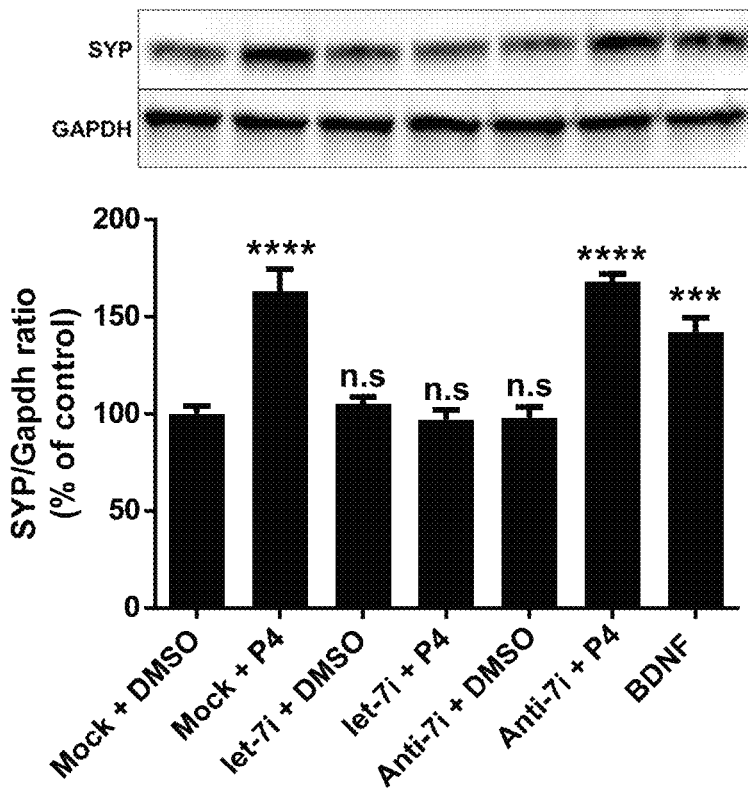

Next, we determined if conditioned media from the different experimental groups represented in FIGS. 10A-10C resulted in changes in expression of synaptophysin, a pre-synaptic marker closely linked to synaptogenesis (4). We observed that conditioned media derived from P4-treated astrocytes (P4-ACM) resulted in a robust increase in SYP (green) immunofluorescence (FIG. 10A), relative to neurons treated with conditioned media from DMSO-treated, and mock-transfected astrocytes. Quantitative analysis revealed that P4-ACM significantly increased both SYP protein level (FIG. 10C) and the number of SYP puncta (FIG. 10B). The same observations were seen in the positive control group (consisting of direct application of BDNF (50 ng/ml) to the primary neuronal cultures). Application of conditioned media collected from P4-treated astrocytes that overexpressed let-7i (group label: let-7i+P4), however, failed to elicit the increase in synaptophysin expression.

Figure 11A:
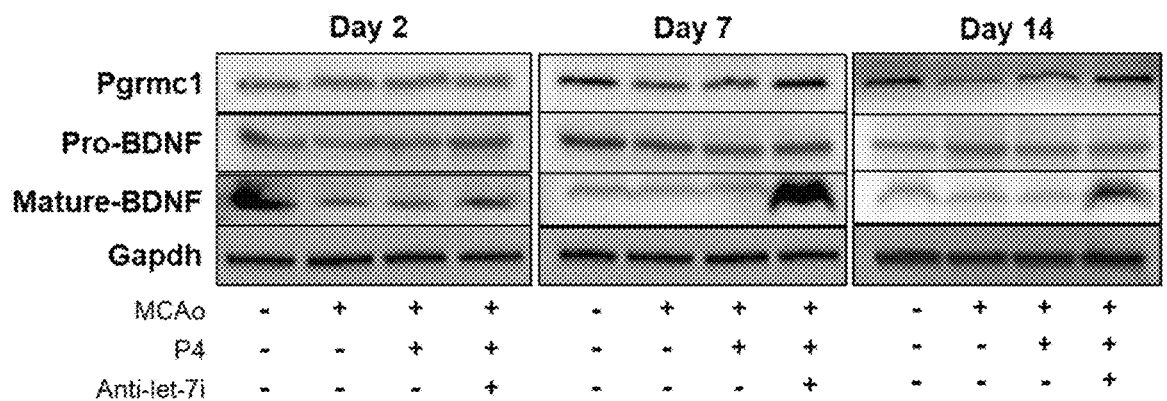
FIGS. 11A-11E: Combined treatment with progesterone (P4) and the let-7i inhibitor reversed ischemia-induced suppression of Pgrmc1 and BDNF expressions in the penumbra.
Figure 11B:
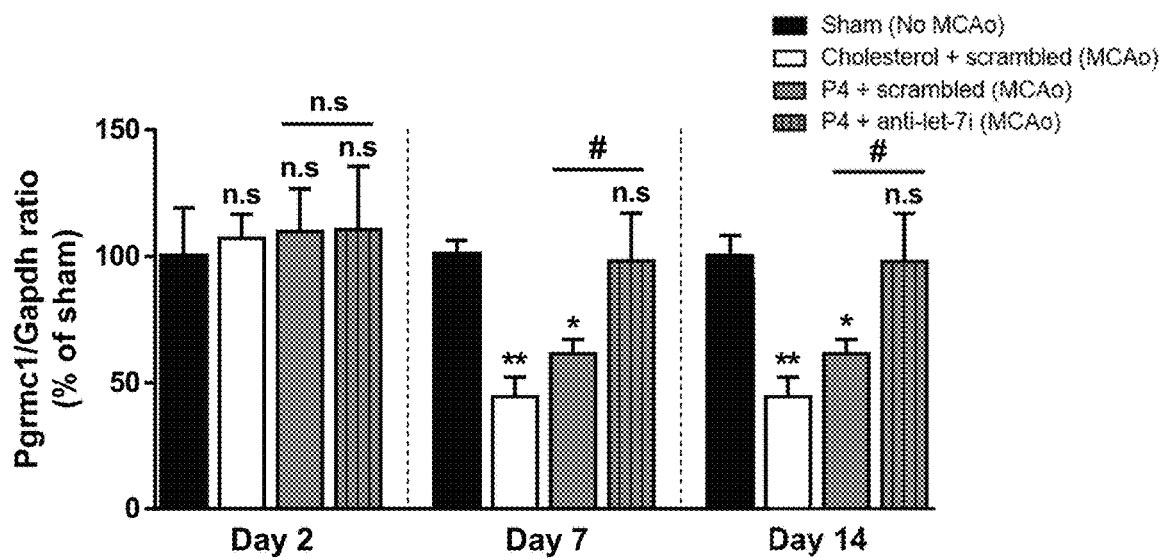
Figure 11C:
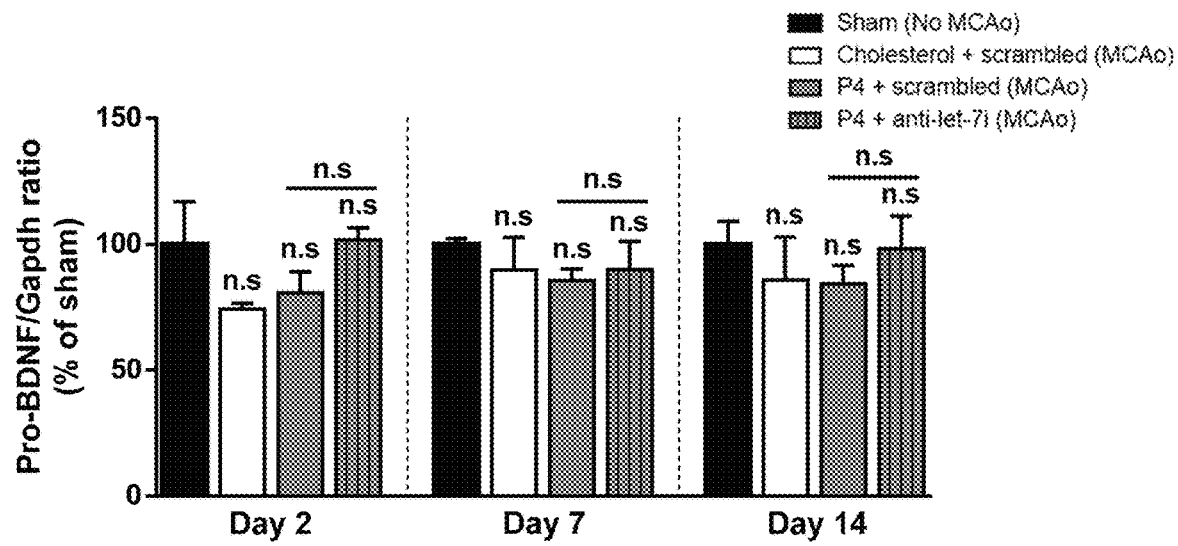
Figure 11D:
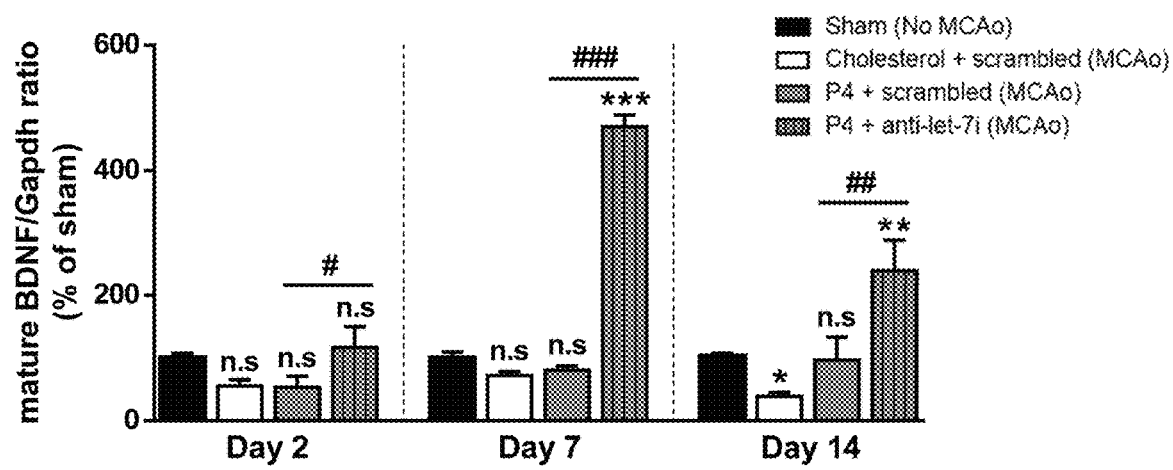
Figure 11E:
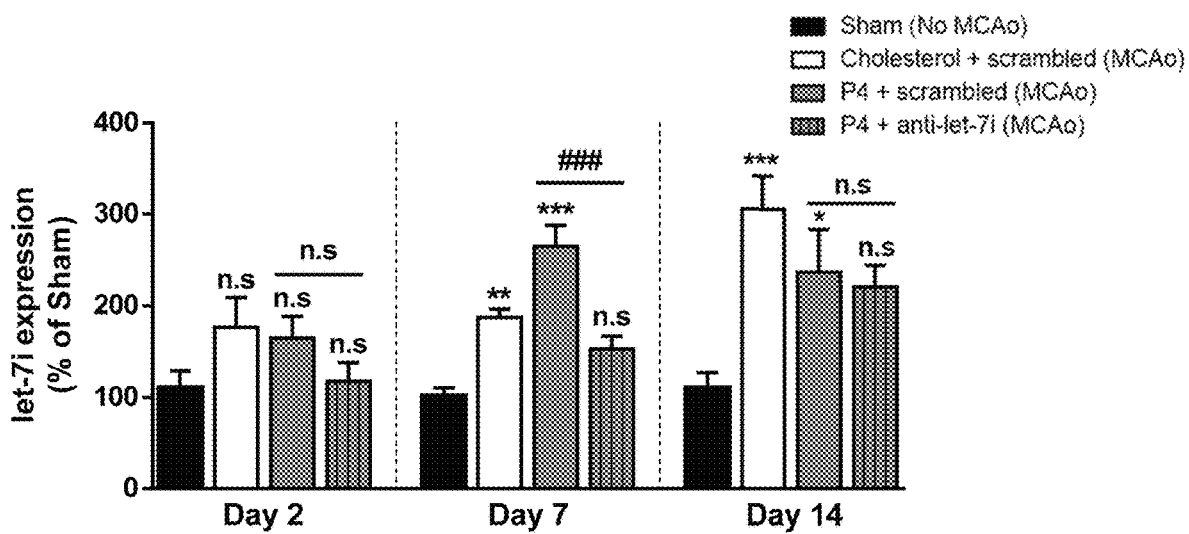

Combined Treatment of Progesterone (P4) and Let-7i Inhibition Alleviate Ischemia-Induced Suppression of Pgrmc1 and BDNF Expressions in the Penumbra of the Ischemic Brain:

We next determined the expression of let-7i in the middle cerebral artery occlusion model of ischemic stroke, focusing on changes in the penumbra. Assessments of let-7i expression were conducted at different time points—2, 7 and 14 days following stroke. Representative images of immunoblots probed for Pgrmc1, along with pro- and mature-BDNF, are shown in FIG. 11A. We found that compared to sham (non-stroked controls), ischemic injury resulted in an up-regulation of let-7i expression (FIG. 11E), starting at day 7 and remained elevated up to 14 days following stroke. P4 treatment alone (P4+a control sequence for let-7i (scrambled)) did not attenuate the stroke-induced increase in Let-7i. As expected, ischemia-induced-increase in let-7i expression was repressed in the group receiving combined treatment P4 and let-7i inhibition (P4+anti-7i) (FIG. 11E). Importantly, along with upregulating let-7i level, ischemia also resulted in a reduction of Pgrmc1 protein level observed at day 7 and day 14 (FIG. 11B). P4 treatment alone did not restore Pgrmc1 level at either of the two time points. Combined treatment (P4+anti-let-7i), however, reversed ischemia-induced suppression of Pgrmc1 protein levels. Furthermore, expression of mature BDNF was reduced as a consequence of stroke at the 14 days post stroke evaluation period (FIG. 11D), while pro-BDNF levels (FIG. 11C) remained unchanged across all time points and all treatments. Compared to sham, the treatment of P4 alone was able to maintain the same level of mature BDNF, even at 14 days post stroke. Remarkably, combined treatment (P4+anti-let-7i) led to a robust increase in expression of mature BDNF observed at day 7 and day 14.

Figure 12A:
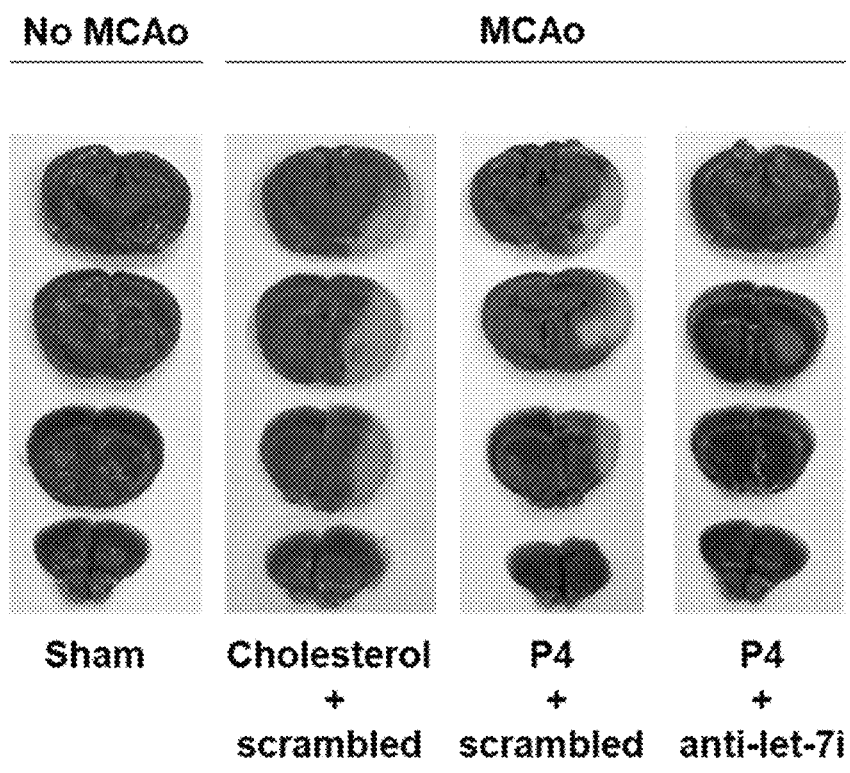
FIGS. 12A-12B: Co-administration of let-7i antagomir (anti-let-7i) and progesterone (P4) reduces ischemic injury.
Figure 12B:
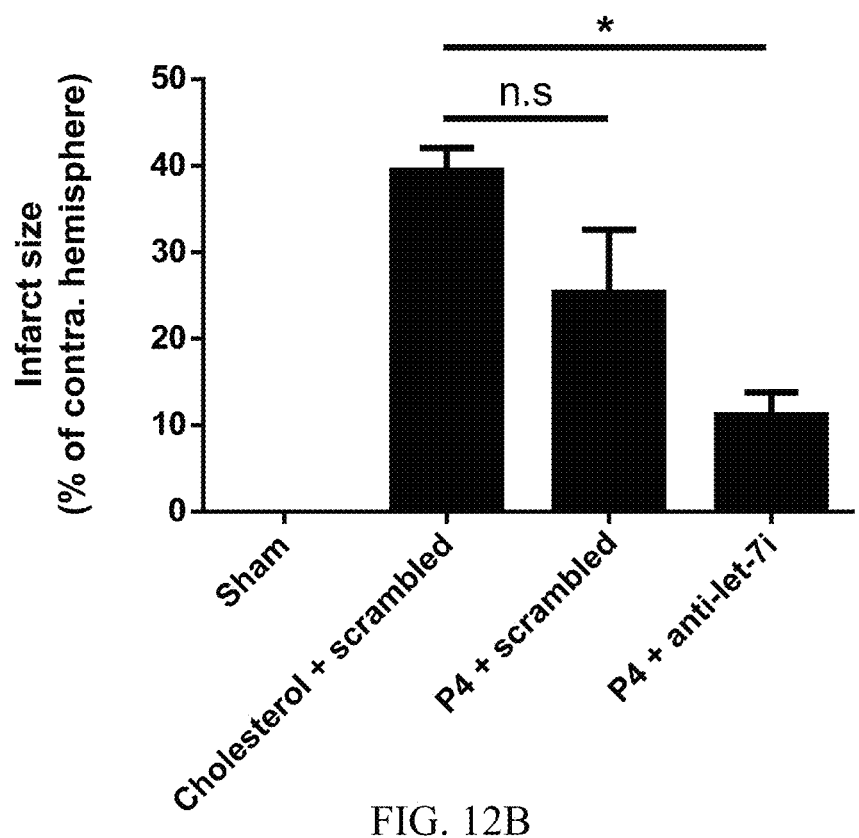

Combined Treatment of Progesterone (P4) and Let-7i Inhibition Reduces Ischemic Injury and Enhances Functional Recovery:

To examine the effect of P4 with or without the let-7i antagomir on the extent of ischemic injury, we utilized 2,3,5-Triphenyltetrazolium chloride (TTC) staining to visualize the size of the ischemic lesion. Representative images of TTC stained are shown in FIG. 12A. Quantification of relative infarct size (FIG. 12B) revealed that the combined treatment (P4+anti-let-7i) significantly reduced ischemic injury; whereas P4 treatment alone did not.

Figure 13:
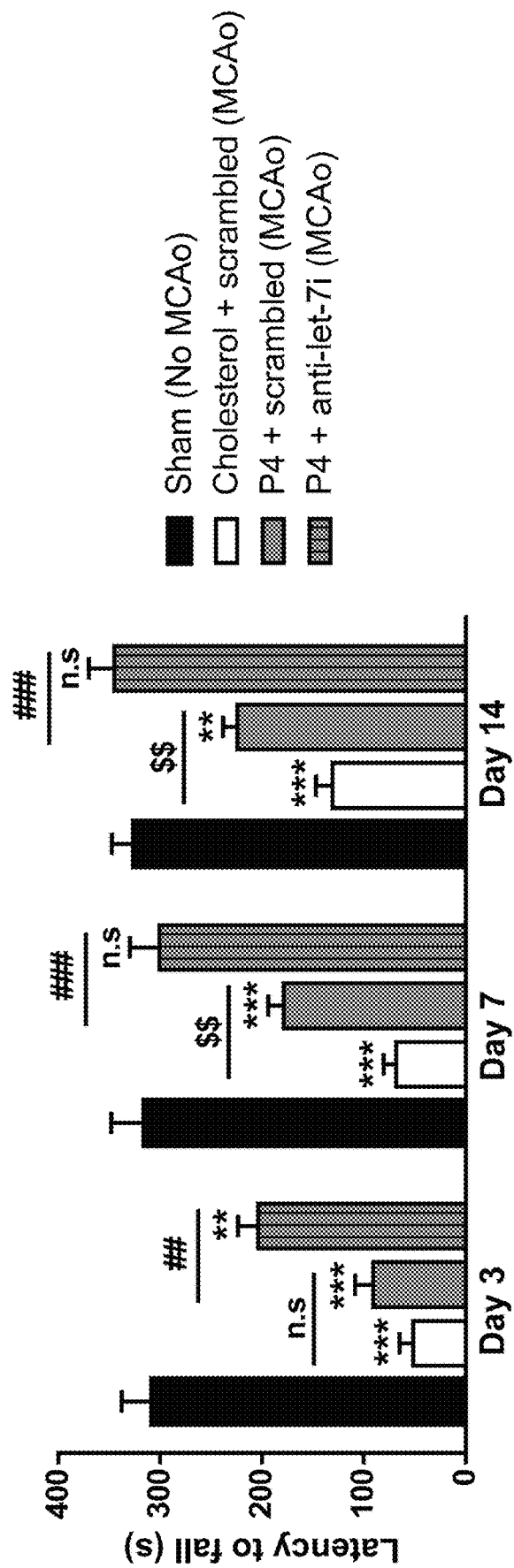
FIG. 13: Co-administration of let-7i antagomir (anti-let-7i) and progesterone (P4) enhances recovery of motor function/grip strength following stroke. Results of wire suspension test at day 3, 7 and 14 post stroke (n=15-20 per group). n.s: not significant, *$P<0.001$ and  $P<0.01$ compared to sham, ### $P<0.001$, ##$P<0.01$ compared to P4+scrambled, and $$$P<0.01$ compared to cholesterol+scrambled. Data are presented as the mean±SEM.

Motor function (grip strength) was also evaluated using the wire suspension test. Results (FIG. 13) showed that compared to the vehicle group (DMSO+scrambled), treatment of P4 led to a partial recovery of motor function, observed on day 7 and day 14. Interestingly, the combined treatment of P4 and the let-7i antagomir resulted in a rapid, but partial, motor function recovery as early as 3 days post-treatment. By day 7, combined treatment led to complete functional recovery, and the improvement was still evident at day 14. Results from FIGS. 12A-12B and FIG. 13 support our hypothesis that let-7i inhibition enhances P4's neuroprotective effects that importantly, enhances functional recovery.

Figure 14A:
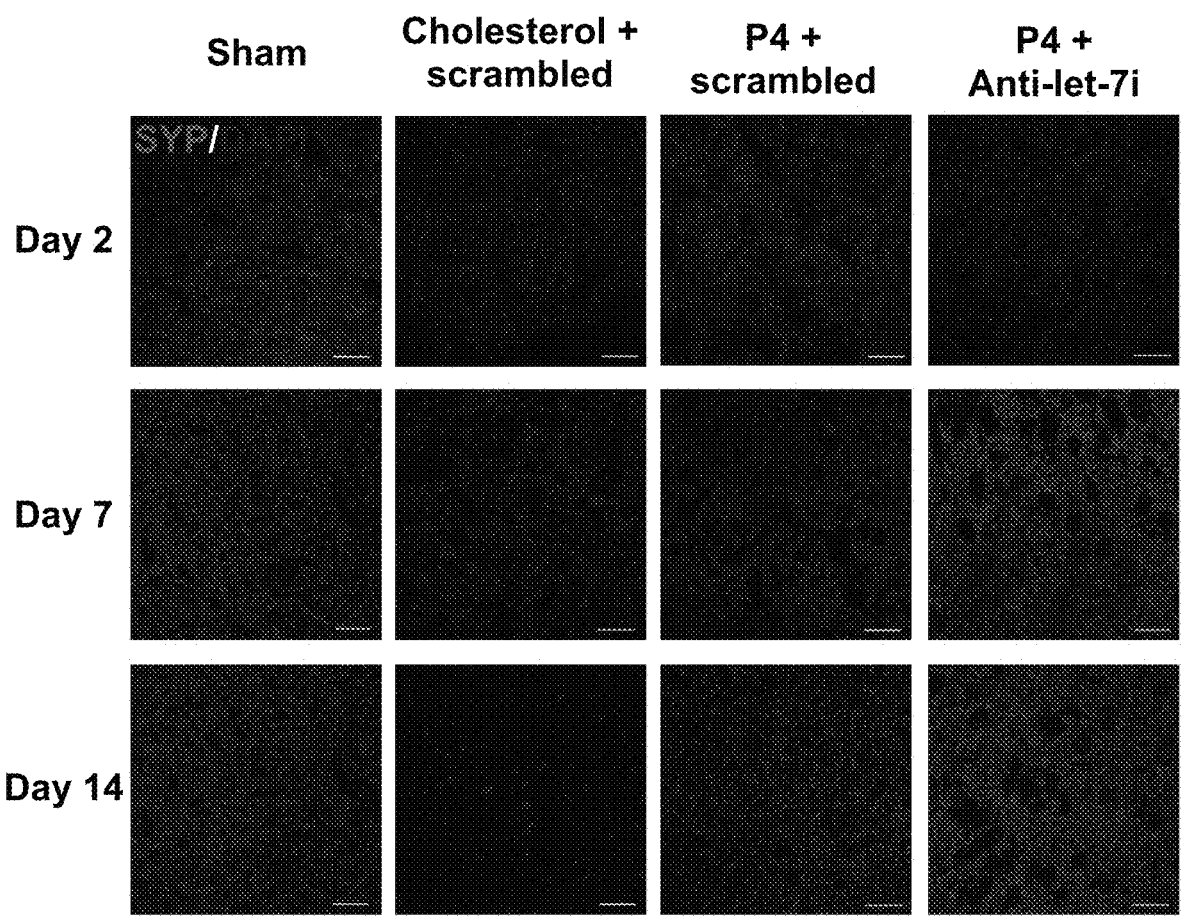
FIGS. 14A-14D: Inhibition of let-7i enhances progesterone (P4)'s effect on the expression of synaptophysin in the penumbra.
Figure 14B:
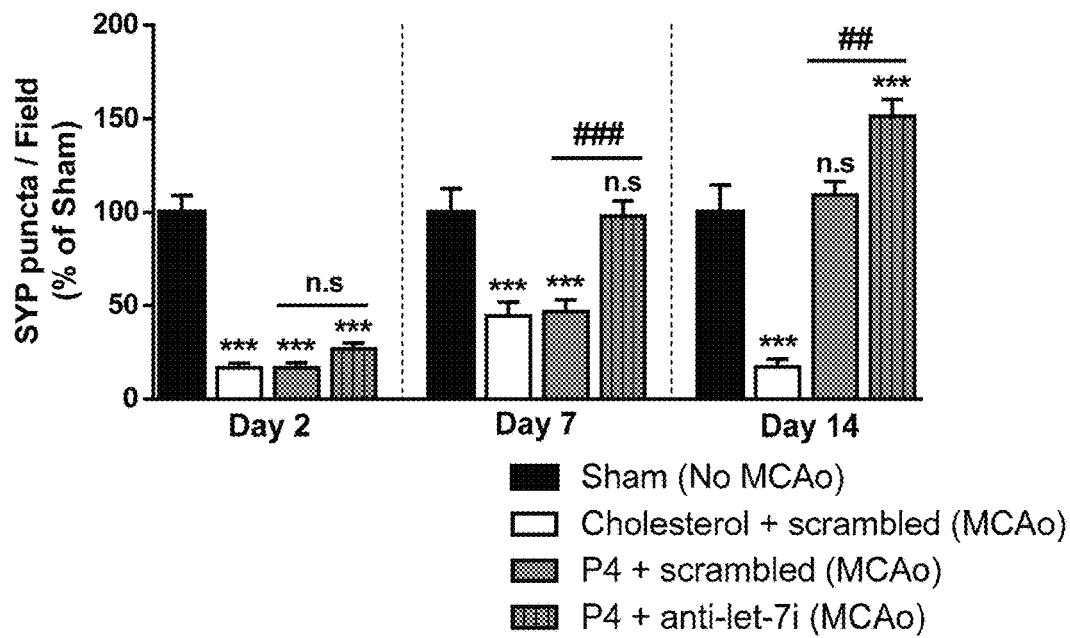
Figure 14C:
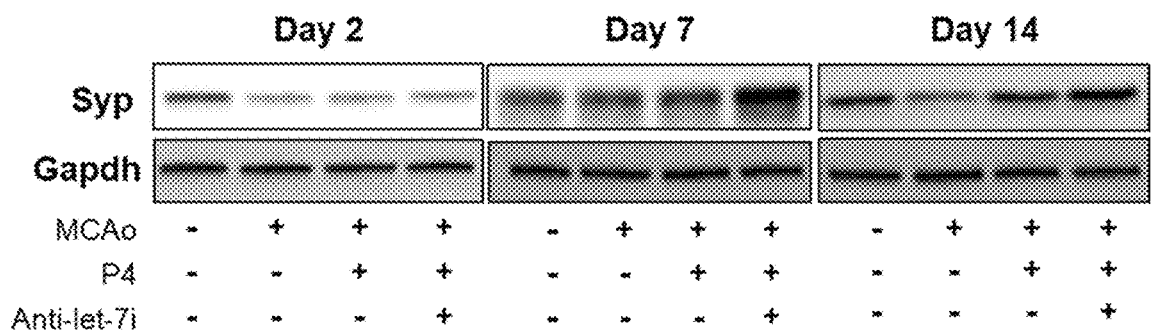
Figure 14D:
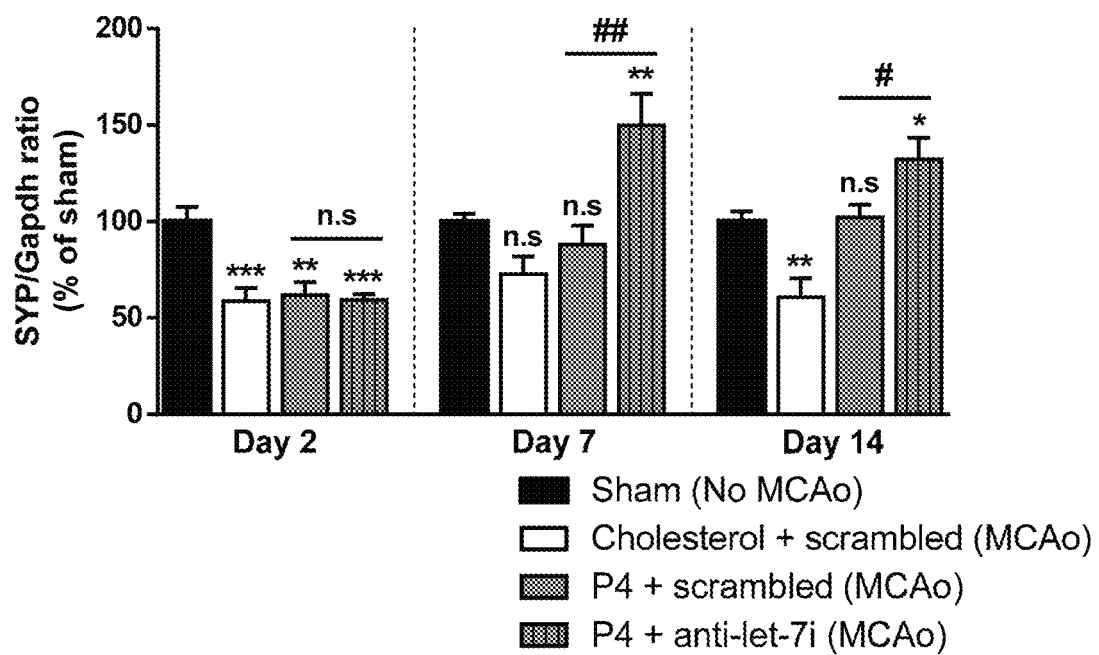

Inhibition of Let-7i Enhances Progesterone (P4)'s Effect on a Synaptogenic Marker:

Synaptic plasticity in the ischemic penumbra region has long been known to influence the functional recovery after stroke (21, 23, 38). Therefore, to determine whether synaptogenesis occurring in the penumbra could be a factor contributing to functional recovery observed in FIG. 13, we extended our in vitro findings, to evaluate the expression of synaptophysin (SYP), a synaptogenic marker, in the penumbra of stroked mice. To do so, we performed immunofluorescence to visualize SYP expression (red) (FIG. 14A) and quantified the relative number of SYP puncta, which is an indication of potential synapses (FIG. 14B). In parallel, Western blot analysis was performed to evaluate total SYP protein levels. Representative immunoblots probed for SYP are shown in FIG. 14C, and its relative quantification of protein level is depicted in FIG. 14D. Results revealed that ischemia resulted in a sustained downregulation of synaptophysin puncta (FIG. 14B) in the penumbra at day 2,7 and 14 post-stroke. In addition, ischemic injury led to decreased SYP protein level at day 2 and 14. There was a transient increase in SYP expression at day 7, which could be due to a compensatory response to the ischemic injury. P4 treatment alone led to a delayed, but sustained, restoration in SYP total protein expression, observed at day 7 and day 14. With regards to the number of SYP puncta, the positive effect of P4 was only evident at day 14 post-treatment. Interestingly, at day 7 and 14, combined treatment (P4+anti-let-7i) resulted in significantly higher expression of SYP, compared to sham controls and P4 treatment alone. This combined treatment also led to a complete restoration of synaptophysin puncta at day 7, an effect that was further enhanced at day 14. Taken together, these findings indicate that P4 induces synaptogenesis in the penumbra of ischemic brain and that let-7i inhibition further enhances this beneficial function of P4.

All patents, patent applications, provisional applications, and publications referred to or cited herein are incorporated by reference in their entirety, including all figures and tables, to the extent they are not inconsistent with the explicit teachings of this specification.

REFERENCES

1. Lisabeth, L. and C. Bushnell, *Stroke risk in women: the role of menopause and hormone therapy*. Lancet Neurol, 2012. 11(1): p. 82-91.
2. Atif, F., et al., *Combination treatment with progesterone and vitamin D hormone is more effective than monotherapy in ischemic stroke: the role of BDNF/TrkB/Erk1/2 signaling in neuroprotection*. Neuropharmacology, 2013. 67: p. 78-87.
3. Ishrat, T., et al., *Effects of progesterone administration on infarct volume and functional deficits following permanent focal cerebral ischemia in rats*. Brain Res, 2009. 1257: p. 94-101.
4. Zhao, Y., et al., *Progesterone influences postischemic synaptogenesis in the CA1 region of the hippocampus in rats*. Synapse, 2011. 65(9): p. 880-91.
5. Kaur, P., et al., *Progesterone increases brain-derived neuroptrophic factor expression and protects against glutamate toxicity in a mitogen-activated protein kinase-and phosphoinositide-3 kinase-dependent manner in cerebral cortical explants*. J Neurosci Res, 2007. 85(11): p. 2441-9.
6. Causing, C. G., et al., *Synaptic innervation density is regulated by neuron-derived BDNF*. Neuron, 1997. 18(2): p. 257-67.
7. Coffey, E. T., K. E. Akerman, and M. J. Courtney, *Brain derived neurotrophic factor induces a rapid upregulation of synaptophysin and tau proteins via the neurotrophin receptor TrkB in rat cerebellar granule cells*. Neurosci Lett, 1997. 227(3): p. 177-80.
8. Heldt, S. A., et al., *Hippocampus-specific deletion of BDNF in adult mice impairs spatial memory and extinction of aversive memories*. Mol Psychiatry, 2007. 12(7): p. 656-70.
9. Franke, H., et al., *Pathophysiology of astroglial purinergic signalling*. Purinergic Signal, 2012. 8(3): p. 629-57.
10. Su, C., et al., *Progesterone increases the release of brain-derived neurotrophic factor from glia via progesterone receptor membrane component 1 (Pgrmc1)-dependent ERK5 signaling*. Endocrinology, 2012. 153(9): p. 4389-400.
11. Intlekofer, K. A. and S. L. Petersen, *Distribution of mRNAs encoding classical progestin receptor, progesterone membrane components 1 and 2, serpine mRNA binding protein 1, and progestin and ADIPOQ receptor family members 7 and 8 in rat forebrain*. Neuroscience, 2011. 172: p. 55-65.
12. Qin, Y., et al., *Progesterone attenuates Abeta25-35-induced neuronal toxicity via JNK inactivation and progesterone receptor membrane component 1-dependent inhibition of mitochondrial apoptotic pathway*. J Steroid Biochem Mol Biol, 2015. 154: p. 302-11.
13. Wessel, L., et al., *Long-term incubation with mifepristone (MLTI) increases the spine density in developing Purkinje cells: new insights into progesterone receptor mechanisms*. Cell Mol Life Sci, 2014. 71(9): p. 1723-40.
14. Mozaffarian, D., et al., *Heart disease and stroke statistics—2015 update: a report from the American Heart Association*. Circulation, 2015. 131(4): p. e29-322.
15. Jodhka, P. K., et al., *The differences in neuroprotective efficacy of progesterone and medroxyprogesterone acetate correlate with their effects on brain-derived neurotrophic factor expression*. Endocrinology, 2009. 150(7): p. 3162-8.
16. Liu, L., et al., *The neuroprotective effects of Tanshinone HA are associated with induced nuclear translocation of TORC1 and upregulated expression of TORC1, pCREB and BDNF in the acute stage of ischemic stroke*. Brain Res Bull, 2010. 82(3-4): p. 228-33.
17. Sato, Y., et al., *White matter activated glial cells produce BDNF in a stroke model of monkeys*. Neurosci Res, 2009. 65(1): p. 71-8.
18. McAllister, A. K., *Dynamic aspects of CNS synapse formation*. Annu Rev Neurosci, 2007. 30: p. 425-50.
19. Sheng, M. and C. C. Hoogenraad, *The postsynaptic architecture of excitatory synapses: a more quantitative view*. Annu Rev Biochem, 2007. 76: p. 823-47.
20. Waites, C. L., A. M. Craig, and C. C. Garner, *Mechanisms of vertebrate synaptogenesis*. Annu Rev Neurosci, 2005. 28: p. 251-74.
21. Stroemer, R. P., T. A. Kent, and C. E. Hulsebosch, *Neocortical neural sprouting, synaptogenesis, and behavioral recovery after neocortical infarction in rats*. Stroke, 1995. 26(11): p. 2135-44.
22. Liu, H. S., et al., *Post-treatment with amphetamine enhances reinnervation of the ipsilateral side cortex in stroke rats*. Neuroimage, 2011. 56(1): p. 280-9.
23. Zhang, L., et al., *Delayed administration of human umbilical tissue-derived cells improved neurological functional recovery in a rodent model of focal ischemia*. Stroke, 2011. 42(5): p. 1437-44.
24. Zhang, L., et al., *Intravenous administration of human umbilical tissue-derived cells improves neurological function in aged rats after embolic stroke*. Cell Transplant, 2012.
25. Goodman, Y., et al., *Estrogens attenuate and corticosterone exacerbates excitotoxicity, oxidative injury, and amyloid beta peptide toxicity in hippocampal neurons*. J Neurochem, 1996. 66(5): p. 1836-44.
26. Cekic, M., I. Sayeed, and D. G. Stein, *Combination treatment with progesterone and vitamin D hormone may be more effective than monotherapy for nervous system injury and disease*. Front Neuroendocrinol, 2009. 30(2): p. 158-72.
27. Micevych, P., G. Bondar, and J. Kuo, *Estrogen actions on neuroendocrine glia*. Neuroendocrinology, 2010. 91(3): p. 211-22.
28. Wong, A. M., et al., *Progesterone influence on neurite outgrowth involves microglia*. Endocrinology, 2009. 150(1): p. 324-32.
29. Gutierrez-Fernandez, M., et al., *Trophic factors and cell therapy to stimulate brain repair after ischaemic stroke*. J Cell Mol Med, 2012. 16(10): p. 2280-90.
30. Madinier, A., et al., *Ipsilateral versus contralateral spontaneous post-stroke neuroplastic changes: involvement of BDNF?* Neuroscience, 2013. 231: p. 169-81.
31. Choi, J. M., et al., *Estradiol increases pre-and post-synaptic proteins in the CA1 region of the hippocampus in female rhesus macaques (Macaca mulatta)*. Endocrinology, 2003. 144(11): p. 4734-8.
32. Tournell, C. E., R. A. Bergstrom, and A. Ferreira, *Progesterone-induced agrin expression in astrocytes modulates glia-neuron interactions leading to synapse formation*. Neuroscience, 2006. 141(3): p. 1327-38.

33. Tsutsui, K., *Neurosteroids in the Purkinje cell: biosynthesis, mode of action and functional significance*. Mol Neurobiol, 2008. 37(2-3): p. 116-25.
34. Stroemer, R. P., T. A. Kent, and C. E. Hulsebosch, *Increase in synaptophysin immunoreactivity following cortical infarction*. Neurosci Lett, 1992. 147(1): p. 21-4.
35. Fu, Z., et al., *Differential roles of Rap1 and Rap2 small GTPases in neurite retraction and synapse elimination in hippocampal spiny neurons*. J Neurochem, 2007. 100(1): p. 118-31.
36. Wendler, A., et al., *Involvement of let-7/miR-98 microRNAs in the regulation of progesterone receptor membrane component 1 expression in ovarian cancer cells*. Oncol Rep, 2011. 25(1): p. 273-9.
37. Stein, D. G. and S. W. Hoffman, *Estrogen and progesterone as neuroprotective agents in the treatment of acute brain injuries*. Pediatr Rehabil, 2003. 6(1): p. 13-22.
38. Sigler, A. and T. H. Murphy, *In vivo 2-photon imaging of fine structure in the rodent brain: before, during, and after stroke*. Stroke, 2010. 41(10 Suppl): p. S117-23.
39. Selvamani, A., et al., *An antagomir to microRNA Let7f promotes neuroprotection in an ischemic stroke model*. PLoS One, 2012. 7(2): p. e32662.
40. Ratka, A. and J. W. Simpkins, *Dose-dependent effects of chronic treatment with estradiol or progesterone on LH secretion in ovariectomized rats*. Endocr Res, 1990. 16(2): p. 165-84.
41. Sun, F., et al., *Ablation of neurogenesis attenuates recovery of motor function after focal cerebral ischemia in middle-aged mice*. PLoS One, 2012. 7(10): p. e46326.
42. Sananbenesi, F., et al., *A hippocampal Cdk5 pathway regulates extinction of contextual fear*. Nat Neurosci, 2007. 10(8): p. 1012-9.
43. Livak, K. J. and T. D. Schmittgen, *Analysis of relative gene expression data using real-time quantitative PCR and the 2(−Delta Delta C(T)) Method*. Methods, 2001. 25(4): p. 402-8.
44. Sun, F., et al. (2016) Pgrmc1/BDNF Signaling Plays a Critical Role in Mediating Glia-Neuron Cross Talk. *Endocrinology* 157(5):2067-2079.
45. Spartalis, E., et al. (2017) The "Yin and Yang" of Platelet-rich Plasma in Breast Reconstruction After Mastectomy or Lumpectomy for Breast Cancer. *Anticancer Res* 37(12):6557-6562.
46. Choudhury, Roy G, et al. (2015) Methylene blue protects astrocytes against glucose oxygen deprivation by improving cellular respiration. *PLoS One* 10(4):e0123096.
47. Rueden, C. T., et al. (2017) ImageJ2: ImageJ for the next generation of scientific image data. *BMC Bioinformatics* 18(1):529.
48. Jala, V. R., et al. (2017) The yin and yang of leukotriene B4 mediated inflammation in cancer. *Semin Immunol* 33:58-64.
49. Crouch, S. P., Kozlowski, R., Slater, K. J., & Fletcher, J. (1993) The use of ATP bioluminescence as a measure of cell proliferation and cytotoxicity. *J Immunol Methods* 160(1):81-88.
50. Parker, C. G., et al. (2017) Ligand and Target Discovery by Fragment-Based Screening in Human Cells. *Cell* 168(3):527-541 e529.
51. Ryou, M. G., et al. (2015) Methylene blue-induced neuronal protective mechanism against hypoxia-reoxygenation stress. *Neuroscience* 301:193-203.
52. Jin, K., et al. (2004) Increased hippocampal neurogenesis in Alzheimer's disease. *Proc Natl Acad Sci USA* 101(1):343-347.
53. Singh, M., Meyer, E. M., Millard, W. J., & Simpkins, J. W. (1994) Ovarian steroid deprivation results in a reversible learning impairment and compromised cholinergic function in female Sprague-Dawley rats. *Brain Res* 644(2):305-312.
54. Li, W., et al. (2014) PTEN degradation after ischemic stroke: a double-edged sword. *Neuroscience* 274:153-161.
55. Salvi, V., et al. (2008) Metabolic syndrome in Italian patients with bipolar disorder. *Gen Hosp Psychiatry* 30(4):318-323.
56. Ni, J., et al. (2015) MicroRNA let-7c-5p protects against cerebral ischemia injury via mechanisms involving the inhibition of microglia activation. *Brain Behav Immun* 49:75-85.
57. Yang, S. H., et al. (2001) 17-beta estradiol can reduce secondary ischemic damage and mortality of subarachnoid hemorrhage. *J Cereb Blood Flow Metab* 21(2):174-181.
58. Hauben, U., D'Hooge, R., Soetens, E., & De Deyn, P. P. (1999) Effects of oral administration of the competitive N-methyl-D-aspartate antagonist, CGP 40116, on passive avoidance, spatial learning, and neuromotor abilities in mice. *Brain Res Bull* 48(3):333-341.
59. Ippolito, D. M. & Eroglu, C. (2010) Quantifying synapses: an immunocytochemistry-based assay to quantify synapse number. *J Vis Exp* (45).
60. Kucukdereli, H., et al. (2011) Control of excitatory CNS synaptogenesis by astrocyte-secreted proteins Hevin and SPARC. *Proc Natl Acad Sci USA* 108(32):E440-449.

We claim:

1. A method of treating a stroke in a subject comprising administering one or more antagonist of Let-7i or a composition comprising said Let-7i antagonist to a subject having had a stroke, wherein said Let-7i antagonist is an oligonucleotide.

2. The method according to claim 1, wherein said oligonucleotide antagonist of Let-7i is an antisense oligonucleotide, siRNA, shRNA, antagomir, or interfering RNA that mediates degradation of Let-7i.

3. The method according to claim 1, said method further comprising the administration of progesterone or a composition thereof to said subject.

4. The method according to claim 3, wherein said antagonist of Let-7i or a composition thereof and said progesterone or a composition thereof is/are administered separately, concurrently, or as a single composition.

5. The method according to claim 1, said method further comprising the administration of BDNF or a composition thereof to said subject.

6. The method according to claim 5, wherein said antagonist of Let-7i or a composition thereof and said BDNF or composition thereof is/are administered separately, concurrently, or as a single composition.

7. The method according to claim 1, wherein the oligonucleotide antagonist of Let-7i hybridizes to SEQ ID NO: 1 or SEQ ID NO: 2.

\* \* \* \* \*

UNITED STATES PATENT AND TRADEMARK OFFICE
CERTIFICATE OF CORRECTION

| | |
|---|---|
| PATENT NO. | : 11,230,711 B2 |
| APPLICATION NO. | : 16/639139 |
| DATED | : January 25, 2022 |
| INVENTOR(S) | : Meharvan Singh, Chang Su and Trinh Nguyen |

Page 1 of 1

It is certified that error appears in the above-identified patent and that said Letters Patent is hereby corrected as shown below:

In the Specification

Column 1,
Lines 17-32,
"KB. The entire content of the sequence listing is incorporated herein by reference in its entirety.
CROSS-REFERENCE TO RELATED APPLICATION
This application claims the benefit of US. Provisional Application Ser. No. 62/544,994, filed Aug. 14, 2017, the disclosure of which is hereby incorporated by reference in its entirety, including all figures, tables and amino acid or nucleic acid sequences.
GOVERNMENT SUPPORT
This invention was made with Government support under AG027956 awarded by the National Institutes of Health." should read
--KB. The entire content of the sequence listing is incorporated herein by reference in its entirety.
GOVERNMENT SUPPORT
This invention was made with Government support under AG027956 awarded by the National Institutes of Health.--.

Column 16,
Line 65, "(Mm00492193 ml)," should read --(Mm00492193_ml),--.

Column 24,
Line 7, "*HA are*" should read --*II are*--.

Signed and Sealed this
First Day of November, 2022

Katherine Kelly Vidal
*Director of the United States Patent and Trademark Office*

SEQUENCE LISTING

<160> NUMBER OF SEQ ID NOS: 3

<210> SEQ ID NO 1
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: Mus musculus sequence is identical

<400> SEQUENCE: 1
ugagguagua guuugugcug uu                     22

<210> SEQ ID NO 2

```
<211> LENGTH: 84
<212> TYPE: RNA
<213> ORGANISM: Homo sapiens

<400> SEQUENCE: 2
cuggcugagg uaguaguuug ugcuguuggu cgdguuguga cauugcccgc uguggagaua      60
acugcgcaag cuacugccuu gcua                                            84

<210> SEQ ID NO 3
<211> LENGTH: 85
<212> TYPE: RNA
<213> ORGANISM: Mus musculus

<400> SEQUENCE: 3
cuggcugagg uaguaguuug ugcuguuggu cgdguuguga cauugcccgc uguggagaua      60
acugcgcaag cuacugccuu gcuag                                           85
```